(12) United States Patent
Kershaw

(10) Patent No.: US 10,928,647 B2
(45) Date of Patent: Feb. 23, 2021

(54) THERAPEUTIC TRAINING DEVICE FOR AUTISM

(71) Applicant: Heidi Kershaw, Manhattan Beach, CA (US)

(72) Inventor: Heidi Kershaw, Manhattan Beach, CA (US)

(*) Notice: Subject to any disclaimer, the term of this patent is extended or adjusted under 35 U.S.C. 154(b) by 0 days.

(21) Appl. No.: 16/834,898

(22) Filed: Mar. 30, 2020

(65) Prior Publication Data
US 2020/0306122 A1 Oct. 1, 2020

Related U.S. Application Data

(60) Provisional application No. 62/827,557, filed on Apr. 1, 2019.

(51) Int. Cl.
| *A61H 5/00* | (2006.01) |
| *G02C 11/04* | (2006.01) |
| *G02C 5/00* | (2006.01) |
| *A61B 90/00* | (2016.01) |
| *A61B 5/16* | (2006.01) |
| *G16H 20/70* | (2018.01) |

(52) U.S. Cl.
CPC ............ *G02C 5/001* (2013.01); *A61H 5/00* (2013.01); *G02C 11/04* (2013.01); *A61B 5/163* (2017.08); *A61B 90/361* (2016.02); *A61B 2560/04* (2013.01); *A61H 2201/0188* (2013.01); *A61H 2201/10* (2013.01); *A61H 2201/5007* (2013.01); *A61H 2201/5043* (2013.01); *A61H 2201/5092* (2013.01); *A61H 2201/5097* (2013.01); *A61H 2205/024* (2013.01); *G02C 2202/06* (2013.01); *G16H 20/70* (2018.01)

(58) Field of Classification Search
CPC .. G16H 20/70; A61H 5/00; A61H 2201/0188; A61H 2201/10; A61H 2201/5007; A61H 2201/5043; A61H 2205/024; A61H 2201/5092; A61H 2201/5097; A61B 90/361; A61B 3/0091; A61B 2560/04; A61B 3/0041; A61B 3/0058; A61B 5/163; G02C 3/003; G02C 5/001; G02C 11/04; G02C 2202/06; G09B 5/02
See application file for complete search history.

(56) References Cited

U.S. PATENT DOCUMENTS

| 5,841,507 | A | * | 11/1998 | Barnes | ............... G02C 7/104 351/49 |
| 7,495,835 | B2 | * | 2/2009 | Daley | ............... A41G 7/02 359/630 |
| 2013/0293830 | A1 | * | 11/2013 | Lopez-Garcia | ...... G02C 11/04 351/158 |
| 2017/0102562 | A1 | * | 4/2017 | Ban | ............... G02B 27/017 |
| 2018/0088890 | A1 | * | 3/2018 | Pohl | ............... G06F 3/017 |

FOREIGN PATENT DOCUMENTS

JP   2000066149   *   3/2000   ............ G02C 7/10

* cited by examiner

*Primary Examiner* — George G King
(74) *Attorney, Agent, or Firm* — David R. Conklin; Kirton McConkie

(57) ABSTRACT

A therapeutic training device configured to be worn on the face of a therapist and capable of displaying media content to a patient with ASD, wherein a level of the displayed media content may be adjusted to permit the patient to see the eyes of the therapist through the media content.

18 Claims, 9 Drawing Sheets

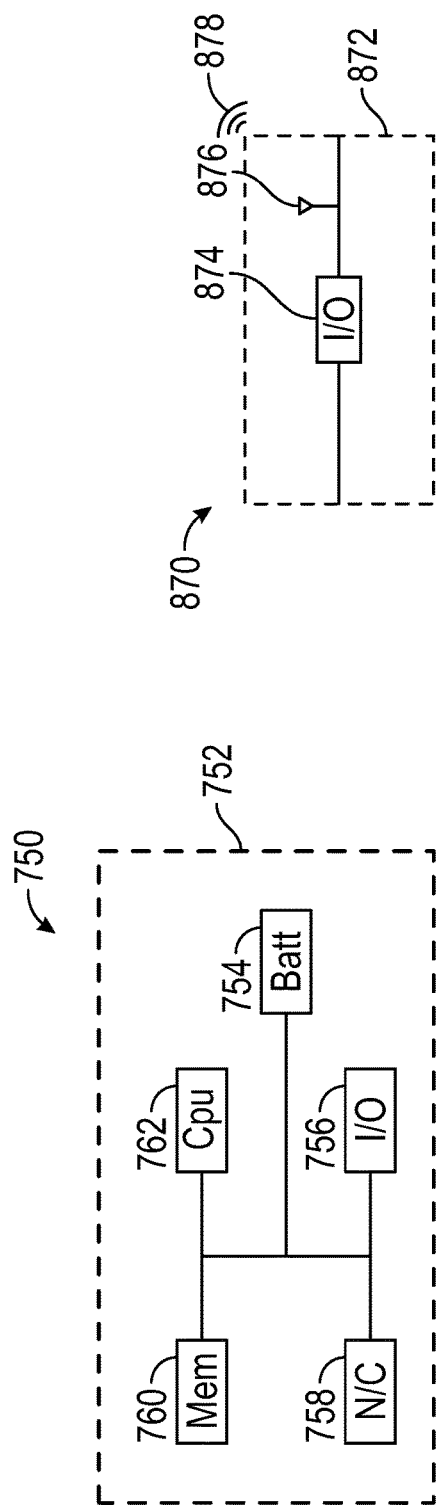
FIG. 8
FIG. 7E
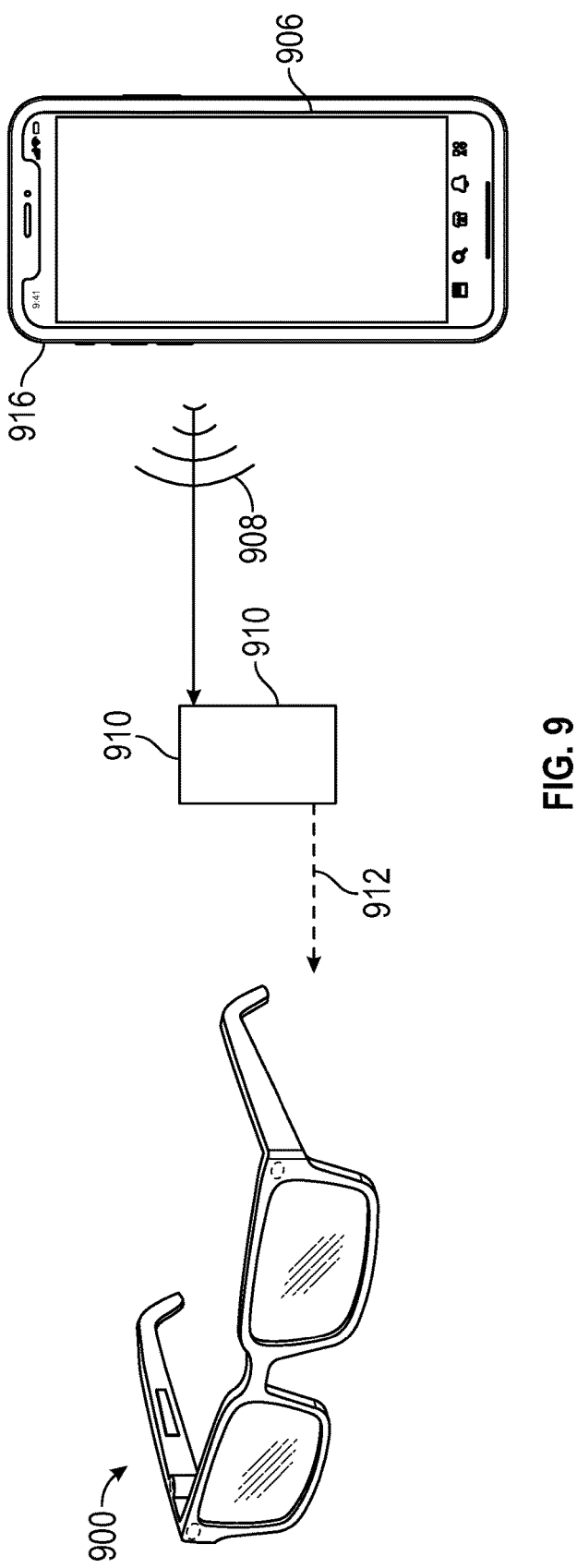
FIG. 9

THERAPEUTIC TRAINING DEVICE FOR AUTISM

FIELD OF THE INVENTION

The present invention relates generally to systems and methods for providing therapeutic training to individuals with autism spectrum disorders (ASD). A therapeutic training device configured to be worn on the face of a therapist and capable of displaying media content to a patient with ASD, wherein a level (i.e., brightness, transparency, and/or opacity) of the media content may be adjusted to permit the patient to see the eyes of the therapist through the media content. The training device is further capable of adjusting a level of the media content so that the eyes of the therapist may increasingly or decreasingly be viewed through the display of media content.

BACKGROUND OF THE INVENTION

Autism spectrum, also known as autism spectrum disorder (ASD) or autism spectrum condition, is a range of neurodevelopmental disorders that include autism, Asperger syndrome and other related conditions. Individuals on the spectrum are often hyper sensitive to sensory stimuli, and present with two types of symptoms, namely, problems in social communication and interactions; and restricted, repetitive patterns of behavior, interests or activities. Long term issues may include difficulties in performing daily tasks, creating and keeping relationships, and maintaining a job.

Research shows that many people with ASD have difficulty with joint attention, which is the ability to share focus on an object or area with another person (Kasari, et al., *J Autism and Dev Disord,* 2010 40(9):1045-1056). Examples of joint attention skills include following someone else's gaze or pointed finger to look at something. Joint attention is important to communication and language learning.

Various studies have also shown that individuals with ASD demonstrate reduced attention to the eye region (Boraston et al., *J Autism Dev Disord,* 2008 38:574-580; Cordon et al., 2008; and Dawson et al., 2005), which in turn limits their ability to interpret and interact with information communicated from the eye region. Recognition of this type of information in others is essential for emotional awareness, following eye-gaze, establishing joint attention, and reading intentions, all of which are hallmark impairments of ASD (Hutchins and Brien, *Research in Autism Spectrum Disord,* 2016 vol. 26). termed "eye-information".

Although various behavioral and developmental therapies exist, no single standard treatment exists for improving joint attention for individuals with ASD. Because the causes and potential cures for ASD are shrouded in uncertainty, many of the treatments intended for ASD merely alleviate problems or symptoms which are either non-existent or have no causal relationship to ASD. Thus, while therapies and treatments currently exist for improving joint attention, challenges still exist. Accordingly, it would be an improvement in the art to augment or even replace current techniques with other techniques.

BRIEF SUMMARY OF THE INVENTION

The present invention relates generally to systems and methods for providing therapeutic training to individuals with autism spectrum disorders (ASD). In particular, the present invention relates to a therapeutic training device that is worn by a therapist, the training device comprising a video display that is positioned over the eyes of the therapist and configured to show media content preferred by an individual with ASD. The training device is further capable of adjusting an opacity of the media content on the video display, whereby the eyes of the therapist may increasingly be viewed through the video display as the opacity of the media content is reduced.

In some aspects of the invention, a therapeutic training device is provided comprising a pair of eyeglasses that are worn by a therapist, wherein the lenses of the eyeglasses comprise a high-transparency video display having a display surface that is viewable by a patient while the therapist is wearing the glasses. The video display may comprise any technology compatible with the teachings of the present invention.

In one aspect of the invention, the video display comprises a plurality of pixels configured to reproduce media content on the display surface, such as a picture or video of interest to a patient with ASD. In some instances, an opacity of at least some of the pixels may be reduced such that the portion of the media content reproduced on these pixels becomes transparent (i.e., loses opacity), thereby permitting the patient to see the eyes of the therapist positioned behind the video display. In some instances, the opacity or transparency of all or substantially all of the pixels of the video display are adjusted in concert with one another, such that an opacity or transparency of the entire media content is uniformly increased or decreased. In other instances, the video display may be divided into regions, the opacity or transparency of which may individually be adjusted, such that an opacity or transparency of one portion of the media content may be less than or greater than an opacity or transparency of a different portion of the media content on the display surface. In some instances, a video display is provided comprising a first region of pixels corresponding to a center portion of the video display, or a portion of the video display that corresponds to a position of the therapist's eye when the glasses are worn, and further comprises a second region of pixels corresponding to a portion of the video display located between the first region and a perimeter edge of the video display. In some instances, a video display is provided have more than three regions of pixels.

In one aspect of the invention, a video display is provided having a plurality of pixels interspersed among a plurality of windows, wherein the windows are incapable of displaying media content. In some instances, the plurality of windows are evenly interspersed among the plurality of pixels. In some instances, the plurality of windows are evenly interspersed among a portion or region of the plurality of pixels. In some instances, the plurality of windows are unevenly interspersed among the plurality of pixels, or among a region of the plurality of pixels. In some instances, the plurality of windows are positioned at a center portion of the video display, or a portion of the video display that corresponds to a position of the therapist's eye when the glasses are worn.

In one aspect of the invention, a video display is provided for displaying media content that projects onto a screen, wherein the screen is configured to reflect the video display such that the media content is viewable by a patient while the therapist is wearing the eye glasses. In some instances, there is also a viewable pathway through the screen. In some instances, a brightness or brightness level of the media content that projects onto the window may be reduced such that the portion of the media content reflected on the window becomes transparent, thereby permitting the patient to see the eyes of the therapist positioned behind the video display.

In some instances, pair of eyeglasses may further include a light or several lights, wherein a brightness or brightness level of the light is uniformly increased or decreased to illuminate the face, and in particular the eyes of the therapist. In some instances, brightness levels of the light and the video display are adjusted in concert with one another. In some instances, brightness levels of the light and the video display are adjusted inversely.

In a further aspect of the invention, therapeutic training device includes various circuitry and electrical components to facilitate use of the device. In some instances, the training device comprises a power supply, such as a battery for powering the device. The training device further comprises electrical components and circuitry for receiving and reproducing media content on the video display. In some instances, the training device comprises electrical component and circuitry for wireless transmission, such as receiving media content from a remote server or mobile device, such as a smartphone, as well as wirelessly sending data that may be collected by the training device during use. In some instances, the training device further comprises one or memory modules for storage of media content and collected data, as well as firmware and other software programs configured for use with the training device.

In another aspect of the invention, the therapeutic training device further includes circuitry and electrical components configured to adjust the opacity or transparency of the pixels of the video display. In some instances, these electrical components are controlled by the user directly through the training device or via a wired remote. In some instances, these electrical components are controlled wirelessly by the user, such as through a wireless remote control or a smartphone.

In some instances, these circuitry and electrical components for adjusting the opacity or transparency of the pixels of the video display are controlled by the training device in response to data received by the training device during use. For example, in some aspects of the invention the training device further includes one or more video cameras configured for use with an eye tracking software program, wherein data collected by the eye tracking software program ("eye data") may be used by a software program of the training device to automatically adjust the opacity or transparency of the pixels of the video display.

In some instances, the training device comprises executable code for running a method whereby eye data is used to determine an optimal opacity or transparency level for the pixels of the video display. In some instances, the eye data represents a time period for which the patient's eyes were fixed on the video display of the training device. In some instances, the eye data represents a percentage of time for which the patient's eyes were fixed on the video display of the training device (i.e., eye fixation percentage), wherein the time may be greater than 5 seconds, 5 seconds, 4 seconds, 3 seconds, 2 seconds, 1 second, or less than 1 second. In some embodiments, the eye data represents an accuracy of the patient's eye gaze relative to the video display (i.e., eye gaze accuracy). In some instances, the executable code of the training device further utilizes one or more buffers, such as a time buffer or pixel buffer, to accommodate for natural and/or errant eye movements.

In some instances, an opacity or transparency of the pixels of the video display is inversely proportional to the eye data. For example, if the eye data for a first time period ($t_1$) shows an eye fixation percentage of 20% (i.e., the patient's eyes were fixed on the video display 20% of duration of $t_1$), the training device would automatically adjust the opacity of the video display to 80% (or set the transparency of the pixels to 20%). If the eye data for a second time period ($t_2$) shows an eye fixation percentage of 70%, the training device would automatically adjust the opacity of the video display to 30% (or set the transparency of the pixels to 70%). One having ordinary skill in the art will readily appreciate that various other algorithms may be used to determine and set an optimal opacity or transparency level for the pixels of the video display based on eye data.

In some instances, a therapeutic training device is provided comprising: i) eyeglass frames, ii) a video display positioned within the eyeglass frames, iii) a controller coupled to the video display to control a display of media content on the video display, and iv) a screen configured to reflect the display of media content outwardly such that the display of media content is viewable by a patient when the training device is worn by a therapist. In some instances, the video display is mounted in the eyeglass frames in an orientation such that the display of media content is emitted from the video display in a plane that is generally perpendicular to a line of sight through the screen. The video display may include any compatible source, including but not limited to a video projector, a LCD display, a LED display, or a quantum dot display. In some instances, the screen is mounted in the eyeglass frames in a plane approximately 45 to the orientation of the video display. The screen may comprise any compatible material, including but not limited to a one-way mirror, a dielectric mirror, or a beamsplitter mirror. In some instances, the training device comprises a plurality of screens.

In some instances, a brightness of the video display is adjustable such that a transparency of the screen is variable, and wherein the therapeutic training device further comprises a light having an adjustable brightness and configured to illuminate, wherein a brightness of the light is adjustable to illuminate the eyes of the therapist. In some instances, the training device comprises a controller configured to inversely adjust brightness levels of the video display and the light.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 7E illustrates a display controller in accordance with a representative embodiment of the present invention.

FIG. 8 illustrates an Input/Output (I/O) processor in communication with a remote display controller in accordance with a representative embodiments of the present invention.

FIG. 9 illustrates a therapeutic training device in communication with a mobile computing device via a receiver in accordance with a representative embodiment of the present invention.

DETAILED DESCRIPTION OF THE INVENTION

Figure 1:
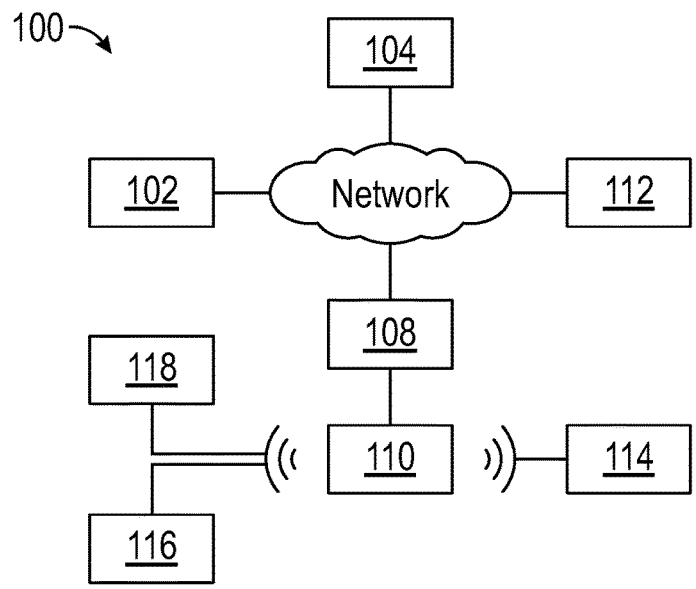
FIG. 1 illustrates a representative network computing environment that provides a suitable operating environment for use of the present invention.

The present invention generally relates to a therapeutic training device configured to be worn on the face of a therapist and capable of displaying media content to a patient with ASD, wherein a brightness and/or opacity of the media content may be adjusted to permit the patient to see the eyes of the therapist through the media content. Any of the features described herein may be combined in order to arrive at a desired configuration in accordance with the explicitly stated and intended operation of the present invention. Use herein of the transitional phrases "in some embodiments" and "in some instances" is not intended to limit the scope of any particular embodiment to a specific feature or set of features disclosed therewith. Rather, the intention of all the various embodiments described herein is to provide frameworks of context in which a specific feature or a set of features may be comprehended and understood in the context of the inventive concept as a whole. Accordingly, the entirety of the present disclosure is to be understood as a body of interchangeable and modular elements that may be selected and combined (in accordance with the requisite purview of one having ordinary skill in the art) to achieve a device, system, or method within the context of the inventive concept, as a whole, disclosed herein.

Embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

As used herein, the term "pixel" is understood to include a minute area of illumination on an electronic display screen or video display, one of many from which an image is composed. Generally, a pixel may include one or more subpixels representing one or more colors, such as red, green, and blue.

As used herein, the term "video display" is understood to include any type of electronic display that is compatible with the present invention. For many embodiments, a compatible video display comprises a full-area two-dimensional display. Non-limiting examples of video displays include LED, LCD, OLED, ELD, E ink, HPA, TFT, OTFT, DLP, SED, FED, Laser TV, carbon nanotubes, IMOD, DMS, AMO-LED, PDP and quantum dot displays.

As used herein, the term "eyeglasses" or "glasses" is understood to include a therapeutic training device adapted to be worn on the face of a therapist such that media content displayed by the training device is positioned over the eye or eyes of the therapist in a manner viewable to a patient. The media content comprises a viewable pathway to enable the therapist to view a patient through the media content while wearing the training device.

As used herein, the term "level of media content" is understood to describe a physical characteristic of media content which may be adjusted to increase or decrease a perceivable amount of the displayed media content on a therapeutic training device disclosed herein, including but not limited to an opacity, a brightness, or a transparency of the displayed media content.

As used herein, the term "transparency" is understood to describe a level of light allowed to pass through a video display of a training device of the present invention and may be represented as a percentage on a transparency scale of 0% to 100%, wherein, for example, 100% transparency describes a condition where 100% of light is allowed to pass through a video display, or a portion of a video display without being scattered (i.e., 0% light scatter), wherein 50% transparency describes a condition where 50% of light is allowed to pass through a video display, or a portion of a video display without being scattered (i.e., 50% light scatter), wherein 20% transparency describes a condition where 20% of light is allowed to pass through a video display, or a portion of a video display without being scattered (i.e., 80% light scatter), and wherein 0% transparency describes a condition where 0% of light is allowed to pass through a video display, or a portion of a video display without being scattered (i.e., 100% light scatter). It should be noted that transparency levels or percentages are based on a maximum attainable transparency for the video display when the opacity level or percentage is 0%. Thus, a transparency percentage of 100% does not represent conditions of 0% light scattering, rather is represents whatever amount of light scattering is present when the opacity level of media content is 0% (i.e., no media content is being reproduced on the video display). A video display of the present invention may be configured to simultaneously provide two or more transparency levels, for example, a first transparency level for the therapist or "inner" side of the video display, and a second transparency level for the patient or "outer" side of the video display.

As used herein, the term "opacity" or "opaque" is understood to describe a level of presence or "fade" of media content data shown on a screen or video display of a training device of the present invention, wherein full opacity of media content data may be termed "unfaded", partial opacity of media content data may be termed "partially faded", and no opacity of media content data may be termed "completely faded". In some instances, opacity of media content may be represented as a percentage on an opacity scale of 0% to 100%, wherein, for example, 100% opacity describes a condition where 100% of media content data is shown on a video display, or a portion of a video display (which would be equivalent to 0% transparency of the video display), wherein 50% opacity describes a condition where 50% of media content data is shown on a video display, or a portion of a video display (which would be equivalent to 50% transparency of the video display), wherein 20% opacity describes a condition wherein 20% of media content data is shown on a video display, or a portion of a video display (which would be equivalent to 80% transparency), and wherein 0% opacity describes a condition where 0% of media content data is shown on a video display, or a portion of a video display (which would be equivalent to 100% transparency of the video display).

As used herein, the terms "brightness", "brightness level(s)" or "level(s) of brightness" are understood to describe the amount of light emitted from a light source (e.g., LED, LED bulb, incandescent bulb), the amount of light emitted from a video display, and/or the amount of light in a reflected image.

As used herein, the term "media content" is understood to include any combination of digital images and videos capable of being reproduced on a video display of the present invention. Media content data may be streamed wirelessly to the therapeutic training device, or may be accessed from on-board memory modules of the training device.

As used herein, the term "eye tracking" is understood to describe the measurement of eye activity of a patient in relation to a therapeutic training device of the present invention.

As used herein, the term "eye data" is understood to describe a measurement of time for which a patient's eyes are fixed on a video display of a training device, and may be represented as a percentage of time on a scale of 0% to 100%, wherein, for example, 0% eye fixation describes a condition where the patient's eyes were fixed on a video display of a training device 0% of a time period, wherein 50% eye fixation describes a condition where the patient's eyes were fixed on a video display of a training device 50% of a time period, wherein 80% eye fixation describes a condition where the patient's eyes were fixed on a video display of a training device 80% of a time period, and wherein 100% eye fixation describes a condition where the patient's eyes were fixed on a video display of a training device 100% of a time period.

As used herein, the term "muscle memory" is understood to describe the ability to reproduce a particular movement without conscious thought, acquired as a result of frequent repetition of that movement. As used herein, the term "muscle memory" is used to describe a therapy whereby an individual with ASD develops the ability to make and maintain eye contact with a therapist through repetitive use of a therapeutic training device of the present invention.

As used herein, the terms "patient", "patient with ASD", and "individual with ASD" are understood to describe a human having a developmental disorder characterized by an inability to make or maintain eye contact with others.

As used herein, the term "therapist" is understood to describe any person wearing a therapeutic training device of the present invention Referring now to FIG. 1, an illustrative environment is shown in which the present invention may be practiced. Not all of the shown components may be required to practice the disclosure, and variations in the arrangement and type of the components may be made without departing from the spirit or scope of the invention. System 100 may include local area networks and wide area networks, shown collectively as network 106, wireless network 110, gateway 108 (which is configured to connect remote and/or different types of networks together), client computing devices 112, 114, 116 and 118, and server computing devices 102 and 104.

Client computing devices may include virtually any device capable of receiving and sending a message over a network, such as wireless network 110, or the like. Such devices include portable devices such as, cellular telephones, smart phones, display pagers, radio frequency (RF) devices, music players, digital cameras, infrared (IR) devices, Personal Digital Assistants (PDAs), handheld computers, laptop computers, wearable computers, tablet computers, integrated devices combining one or more of the preceding devices, or the like. Client device 112 may include virtually any computing device that typically connects using a wired communications medium such as personal computers, multiprocessor systems, microprocessor-based or programmable consumer electronics, network PCs, or the like. In one embodiment, one or more of client devices 112, 114, 116 and 118 may also be configured to operate over a wired and/or a wireless network.

Client devices 112, 114, 116 and 118 may include a wide variety of capabilities and features. For example, a cell phone may have a numeric keypad and a few lines of monochrome LCD display on which only text may be displayed. In another example, a web-enabled client device may have a touch sensitive screen, a stylus, and several lines of color LCD display in which both text and graphic may be displayed.

A web-enabled client device may include a browser application that is configured to receive and to send web pages, web-based messages, or the like. The browser application may be configured to receive and display graphic, text, multimedia, or the like, employing virtually any web based language, including a wireless application protocol messages (WAP), or the like. In one embodiment, the browser application may be enabled to employ one or more of Handheld Device Markup Language (HDML), Wireless Markup Language (WML), WMLScript, JavaScript, Standard Generalized Markup Language (SMGL), HyperText Markup Language (HTML), eXtensible Markup Language (XML), or the like, to display and send information.

Client computing devices 112, 114, 116 and 118 may also include at least one other client application configured to receive content from another computing device, including, without limit, server computing devices 102 and/or 104. The client application may include a capability to provide and receive textual content, multimedia information, or the like. The client application may further provide information that identifies itself, including a type, capability, name, or the like. In some embodiments, client devices 112, 114, 116 and 118 may uniquely identify themselves through any of a variety of mechanisms, including a phone number, Mobile Identification Number (MIN), an electronic serial number (ESN), mobile device identifier, network address, such as IP (Internet Protocol) address, Media Access Control (MAC) layer identifier, or other identifier. The identifier may be provided in a message, or the like, sent to another computing device.

Client computing devices 112, 114, 116 and 118 may also be configured to communicate a message, such as through email, Short Message Service (SMS), Multimedia Message Service (MMS), instant messaging (IM), internet relay chat (IRC), Mardam-Bey's IRC (mIRC), Jabber, or the like, to another computing device. However, the present disclosure is not limited to these message protocols, and virtually any other message protocol may be employed.

Client devices 112, 114, 116 and 118 may further be configured to include a client application that enables the user to log into a user account that may be managed by another computing device. Such user account, for example, may be configured to enable the user to receive emails, send/receive IM messages, SMS messages, access selected web pages, download scripts, applications, or a variety of other content, or perform a variety of other actions over a network. However, managing of messages or otherwise accessing and/or downloading content, may also be performed without logging into the user account. Thus, a user of client devices 112, 114, 116 and 118 may employ any of a variety of client applications to access content, read web pages, receive/send messages, or the like. In one embodiment, for example, the user may employ a browser or other client application to access a web page hosted by a Web server implemented as server computing device 102. In one embodiment, messages received by client computing devices 112, 114, 116 and 118 may be saved in non-volatile memory, such as flash and/or PCM, across communication sessions and/or between power cycles of said client computing devices.

In some embodiments, client devices 114, 116 and 118 may be coupled to network 106 via wireless network 110. Wireless network 110 may include any of a variety of wireless sub-networks that may further overlay stand-alone ad-hoc networks, and the like, to provide an infrastructure-oriented connection for client devices 114, 116 and 118. Such sub-networks may include mesh networks, Wireless LAN (WLAN) networks, cellular networks, and the like. Wireless network 110 may further include an autonomous system of terminals, gateways, routers, and the like connected by wireless radio links, and the like. These connectors may be configured to move freely and randomly and organize themselves arbitrarily, such that the topology of wireless network 110 may change rapidly.

Wireless network 110 may further employ a plurality of access technologies including 2nd (2G), 3rd (3G) generation radio access for cellular systems, WLAN, Wireless Router (WR) mesh, and the like. Access technologies such as 2G, 3G, and future access networks may enable wide area coverage for mobile devices, such as client devices 114, 116 and 118 with various degrees of mobility. For example, wireless network 110 may enable a radio connection through a radio network access such as Global System for Mobil communication (GSM), General Packet Radio Services (GPRS), Enhanced Data GSM Environment (EDGE), WEDGE, Bluetooth, Bluetooth Low Energy (LE), High Speed Downlink Packet Access (HSDPA), Universal Mobile Telecommunications System (UMTS), Wi-Fi, Zigbee, Wideband Code Division Multiple Access (WCDMA), and the like. In essence, wireless network 110 may include virtually any wireless communication mechanism by which information may travel between client devices 102-104 and another computing device, network, and the like.

Network 106 is configured to couple one or more servers depicted in FIG. 1 as server computing devices 102 and 104 and their respective components with other computing devices, such as client device 112, and through wireless network 110 to client devices 114, 116 and 118. Network 106 is enabled to employ any form of computer readable media for communicating information from one electronic device to another. Also, network 106 may include the Internet in addition to local area networks (LANs), wide area networks (WANs), direct connections, such as through a universal serial bus (USB) port, other forms of computer-readable media, or any combination thereof. On an interconnected set of LANs, including those based on differing architectures and protocols, a router acts as a link between LANs, enabling messages to be sent from one to another.

In various embodiments, the arrangement of system 100 includes components that may be used in and constitute various networked architectures. Such architectures may include peer-to-peer, client-server, two-tier, three-tier, or other multi-tier (n-tier) architectures, MVC (Model-View-Controller), and MVP (Model-View-Presenter) architectures among others. Each of these are briefly described below.

Peer to peer architecture entails use of protocols, such as P2PP (Peer To Peer Protocol), for collaborative, often symmetrical, and independent communication and data transfer between peer client computers without the use of a central server or related protocols.

Client-server architectures includes one or more servers and a number of clients which connect and communicate with the servers via certain predetermined protocols. For example, a client computer connecting to a web server via a browser and related protocols, such as HTTP, may be an example of a client-server architecture. The client-server architecture may also be viewed as a 2-tier architecture.

Two-tier, three-tier, and generally, n-tier architectures are those which separate and isolate distinct functions from each other by the use of well-defined hardware and/or software boundaries. An example of the two-tier architecture is the client-server architecture as already mentioned. In a 2-tier architecture, the presentation layer (or tier), which provides user interface, is separated from the data layer (or tier), which provides data contents. Business logic, which processes the data may be distributed between the two tiers.

A three-tier architecture, goes one step farther than the 2-tier architecture, in that it also provides a logic tier between the presentation tier and data tier to handle application data processing and logic. Business applications often fall in and are implemented in this layer.

MVC (Model-View-Controller) is a conceptually many-to-many architecture where the model, the view, and the controller entities may communicate directly with each other. This is in contrast with the 3-tier architecture in which only adjacent layers may communicate directly.

MVP (Model-View-Presenter) is a modification of the MVC model, in which the presenter entity is analogous to the middle layer of the 3-tier architecture and includes the applications and logic.

Communication links within LANs typically include twisted wire pair or coaxial cable, while communication links between networks may utilize analog telephone lines, full or fractional dedicated digital lines including T1, T2, T3, and T4, Integrated Services Digital Networks (ISDNs), Digital Subscriber Lines (DSLs), wireless links including satellite links, or other communications links known to those skilled in the art. Furthermore, remote computers and other related electronic devices could be remotely connected to either LANs or WANs via a modem and temporary telephone link. Network 106 may include any communication method by which information may travel between computing devices. Additionally, communication media typically may enable transmission of computer-readable instructions, data structures, program modules, or other types of content, virtually without limit. By way of example, communication media includes wired media such as twisted pair, coaxial cable, fiber optics, wave guides, and other wired media and wireless media such as acoustic, RF, infrared, and other wireless media.

Figure 2:
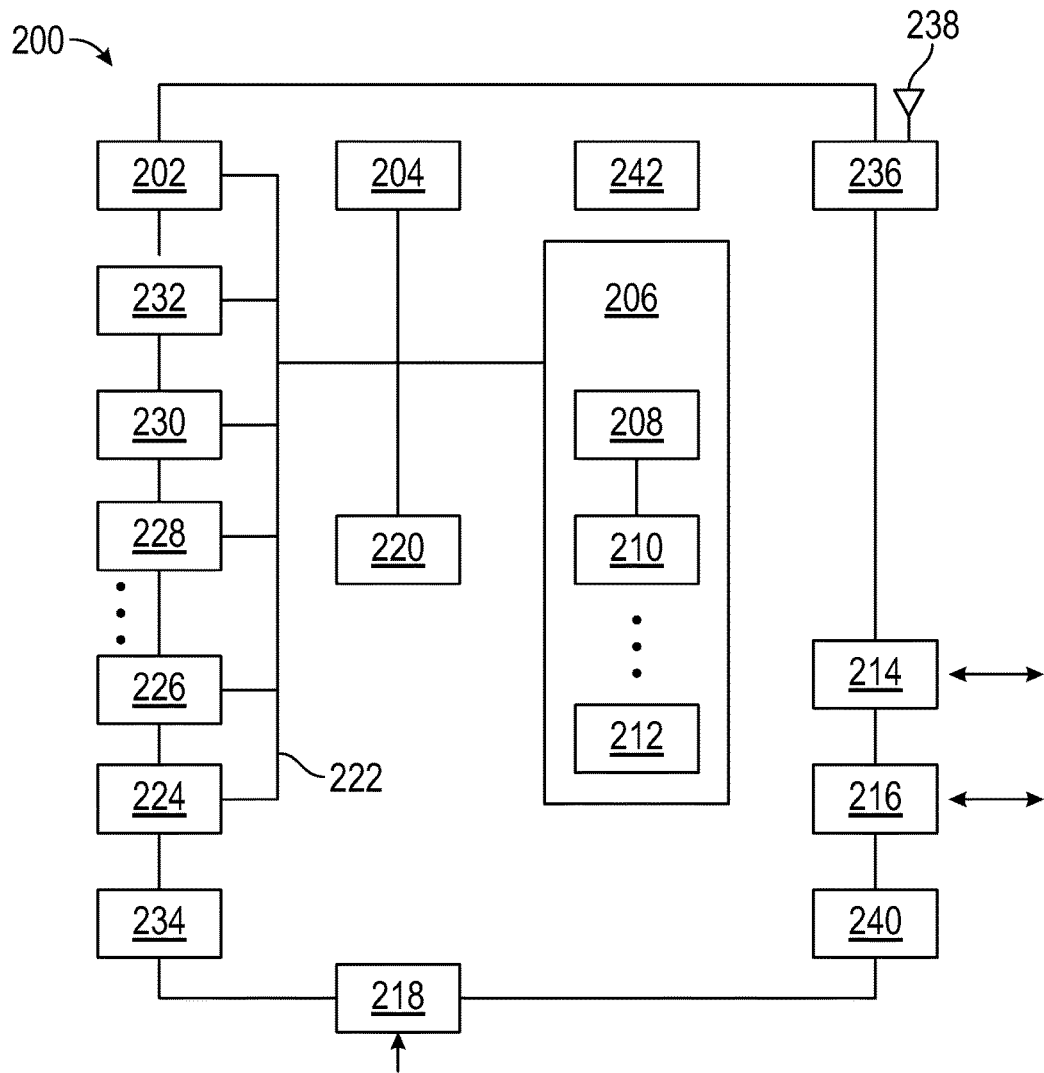
FIG. 2 illustrates a representative computing device that may be used in the network computing environment of FIG. 1.

Referring now to FIG. 2, an illustrative computing device 200 is shown. Computing device 200 may represent any one of the server and/or client computing devices shown in FIG. 1. A computing device represented by computing device 200 may include less or more than all the components shown in FIG. 2, depending on the functionality needed. For example, a mobile computing device may include the transceiver 236 and antenna 238, while a server computing device 102 of FIG. 1 may not include these components. Those skilled in the art will appreciate that the scope of integration of components of computing device 200 may be different from what is shown. As such, some of the components of computing device 200 shown in FIG. 2 may be integrated together as a single unit. For example, NIC 230 and transceiver 236 may be implemented as an integrated unit. Additionally, different functions of a single component may be separated and implemented across several components instead. For example, different functions of I/O processor 220 may be separated into two or more processing units.

With continued reference to FIG. 2, computing device 200 includes optical storage 202, Central Processing Unit (CPU) 204, memory module 206, display interface 214, audio interface 216, input devices 218, Input/Output (I/O) processor 220, bus 222, non-volatile memory 224, various other interfaces 226-228, Network Interface Card (NIC) 320, hard disk 232, power supply 234, transceiver 236, antenna 238, haptic interface 240, and Global Positioning System (GPS) unit 242. Memory module 206 may include software such as Operating System (OS) 208, and a variety of software application programs and/or software modules/components 210 to 212. Such software modules and components may be stand-alone application software or be components, such as DLL (Dynamic Link Library) of a larger application software. Computing device 200 may also include other components not shown. For example, computing device 200 may further include an illuminator (for example, a light), graphic interface, and portable storage media such as USB drives. Computing device 200 may also include other processing units, such as a math co-processor, graphics processor/accelerator, and a Digital Signal Processor (DSP).

Optical storage device 202 may include optical drives for using optical media, such as CD (Compact Disc), DVD (Digital Video Disc), and the like. Optical storage devices 202 may provide inexpensive ways for storing information for archival and/or distribution purposes.

Central Processing Unit (CPU) 204 may be the main processor for software program execution in computing device 200. CPU 204 may represent one or more processing units that obtain software instructions from memory module 206 and execute such instructions to carry out computations and/or transfer data between various sources and destinations of data, such as hard disk 232, I/O processor 220, display interface 214, input devices 218, non-volatile memory 224, and the like.

Memory module 206 may include RAM (Random Access Memory), ROM (Read Only Memory), and other storage means, mapped to one addressable memory space. Memory module 206 illustrates one of many types of computer storage media for storage of information such as computer readable instructions, data structures, program modules or other data. Memory module 206 may store a basic input/output system (BIOS) for controlling low-level operation of computing device 200. Memory module 206 may also store OS 208 for controlling the general operation of computing device 200. It OS 208 may include a general-purpose operating system such as a version of UNIX, or LINUX™, or a specialized client-side and/or mobile communication operating system such as Windows Mobile™, Android®, or the Symbian® operating system. OS 208 may, in turn, include or interface with a Java virtual machine (JVM) module that enables control of hardware components and/or operating system operations via Java application programs.

Memory module 206 may further include one or more distinct areas (by address space and/or other means), which can be utilized by computing device 200 to store, among other things, applications and/or other data. For example, one area of memory module 206 may be set aside and employed to store information that describes various capabilities of computing device 200, a device identifier, and the like. Such identification information may then be provided to another device based on any of a variety of events, including being sent as part of a header during a communication, sent upon request, or the like. One common software application is a browser program that is generally used to send/receive information to/from a web server. In one embodiment, the browser application is enabled to employ Handheld Device Markup Language (HDML), Wireless Markup Language (WML), WMLScript, JavaScript, Standard Generalized Markup Language (SMGL), HyperText Markup Language (HTML), eXtensible Markup Language (XML), and the like, to display and send a message. However, any of a variety of other web based languages may also be employed. In one embodiment, using the browser application, a user may view an article or other content on a web page with one or more highlighted portions as target objects.

Display interface 214 may be coupled with a display unit (i.e., video display), such as liquid crystal display (LCD), gas plasma, light emitting diode (LED), or any other type of display unit that may be used with computing device 200. Display units coupled with display interface 214 may also include a touch sensitive screen arranged to receive input from an object such as a stylus or a digit from a human hand. Display interface 214 may further include interface for other visual status indicators, such Light Emitting Diodes (LED), light arrays, and the like.

Display interface 214 may include both hardware and software components. For example, display interface 214 may include a graphic accelerator for rendering graphic-intensive outputs on the display unit. In one embodiment, display interface 214 may include software and/or firmware components that work in conjunction with CPU 204 to render graphic output on the display unit.

Audio interface 216 is arranged to produce and receive audio signals such as the sound of a human voice. For example, audio interface 216 may be coupled to a speaker and microphone (not shown) to enable communication with a human operator, such as spoken commands, and/or generate an audio acknowledgement for some action.

Input devices 218 may include a variety of device types arranged to receive input from a user, such as a keyboard, a keypad, a mouse, a touchpad, a touch-screen (described with respect to display interface 214), a multi-touch screen, a microphone for spoken command input (describe with respect to audio interface 216), and the like.

I/O processor 220 is generally employed to handle transactions and communications with peripheral devices such as mass storage, network, input devices, display, and the like, which couple computing device 200 with the external world. In small, low power computing devices, such as some mobile devices, functions of the I/O processor 220 may be integrated with CPU 204 to reduce hardware cost and complexity. In one embodiment, I/O processor 220 may the primary software interface with all other device and/or hardware interfaces, such as optical storage 202, hard disk 232, interfaces 226 to 228, display interface 214, audio interface 216, and input devices 218.

An electrical bus 222 internal to computing device 200 may be used to couple various other hardware components, such as CPU 204, memory module 206, I/O processor 220, and the like, to each other for transferring data, instructions, status, and other similar information.

Non-volatile memory 224 may include memory built into computing device 200, or portable storage medium, such as USB drives that may include PCM arrays, flash memory including NOR and NAND flash, pluggable hard drive, and the like. In one embodiment, portable storage medium may behave similarly to a disk drive. In another embodiment, portable storage medium may present an interface different than a disk drive, for example, a read-only interface used for loading/supplying data and/or software.

Various other interfaces 226 to 228 may include other electrical and/or optical interfaces for connecting to various hardware peripheral devices and networks, such as IEEE 1394 also known as FireWire, Universal Serial Bus (USB), Small Computer Serial Interface (SCSI), parallel printer interface, Universal Synchronous Asynchronous Receiver Transmitter (USART), Video Graphics Array (VGA), Super VGA (SVGA), and the like.

Network Interface Card (NIC) 230 may include circuitry for coupling computing device 200 to one or more networks, and is generally constructed for use with one or more communication protocols and technologies including, but not limited to, Global System for Mobile communication (GSM), code division multiple access (CDMA), time division multiple access (TDMA), user datagram protocol (UDP), transmission control protocol/Internet protocol (TCP/IP), SMS, general packet radio service (GPRS), WAP, ultra wide band (UWB), IEEE 802.16 Worldwide Interoperability for Microwave Access (WiMax), SIP/RTP, Bluetooth, Wi-Fi, Zigbee, UMTS, HSDPA, WCDMA, WEDGE, or any of a variety of other wired and/or wireless communication protocols.

Hard disk 232 is generally used as a mass storage device for computing device 200. In one embodiment, hard disk 232 may be a Ferro-magnetic stack of one or more disks forming a disk drive embedded in or coupled to computing device 200. In another embodiment, hard drive 232 may be implemented as a solid-state device configured to behave as a disk drive, such as a flash-based hard drive. In yet another embodiment, hard drive 232 may be a remote storage accessible over network interface 230 or another interface 226, but acting as a local hard drive. Those skilled in the art will appreciate that other technologies and configurations may be used to present a hard drive interface and functionality to computing device 200 without departing from the spirit of the present disclosure.

Power supply 234 provides power to computing device 200. A rechargeable or non-rechargeable battery may be used to provide power. The power may also be provided by an external power source, such as an AC adapter or a powered docking cradle that supplements and/or recharges a battery.

Transceiver 236 generally represents transmitter/receiver circuits for wired and/or wireless transmission and receipt of electronic data. Transceiver 236 may be a stand-alone module or be integrated with other modules, such as NIC 230. Transceiver 236 may be coupled with one or more antennas for wireless transmission of information.

Antenna 238 is generally used for wireless transmission of information, for example, in conjunction with transceiver 236, NIC 230, and/or GPS 242. Antenna 238 may represent one or more different antennas that may be coupled with different devices and tuned to different carrier frequencies configured to communicate using corresponding protocols and/or networks. Antenna 238 may be of various types, such as omni-directional, dipole, slot, helical, and the like.

Haptic interface 240 is configured to provide tactile feedback to a user of computing device 200. For example, the haptic interface may be employed to vibrate computing device 200, or an input device coupled to computing device 200, such as a game controller, in a particular way when an event occurs, such as hitting an object with a car in a video game.

Global Positioning System (GPS) unit 242 can determine the physical coordinates of computing device 200 on the surface of the Earth, which typically outputs a location as latitude and longitude values. GPS unit 242 can also employ other geo-positioning mechanisms, including, but not limited to, triangulation, assisted GPS (AGPS), E-OTD, CI, SAI, ETA, BSS or the like, to further determine the physical location of computing device 200 on the surface of the Earth. It is understood that under different conditions, GPS unit 242 can determine a physical location within millimeters for computing device 200. In other cases, the determined physical location may be less precise, such as within a meter or significantly greater distances. In one embodiment, however, a mobile device represented by computing device 200 may, through other components, provide other information that may be employed to determine a physical location of the device, including for example, a MAC (Media Access Control) address.

Figure 3:
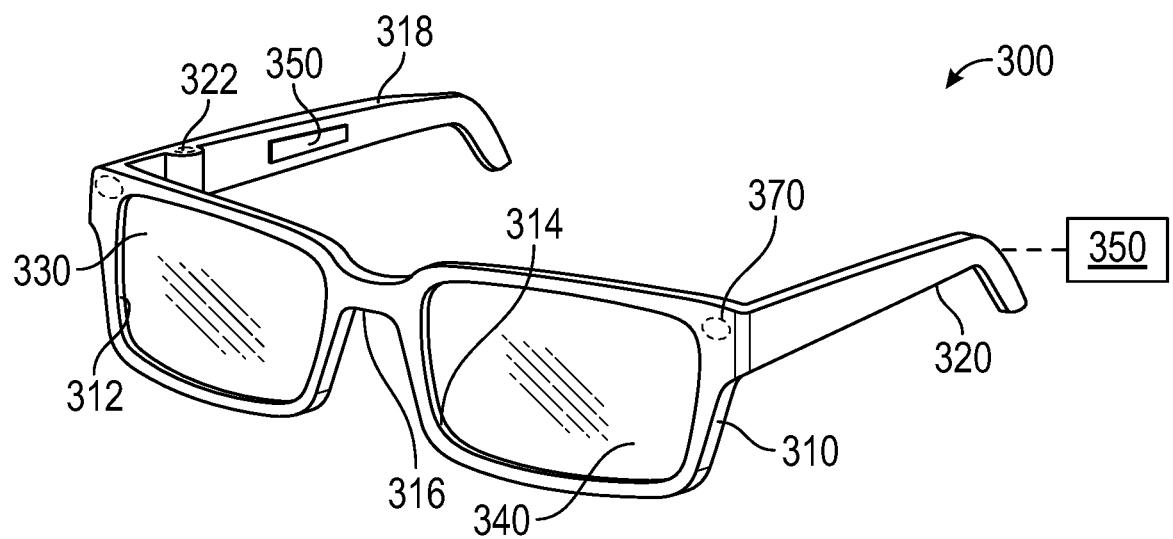
FIG. 3 illustrates a perspective view of a therapeutic training device in accordance with a representative embodiment of the present invention.

Referring now to FIG. 3, a therapeutic training device 300 is shown with configurable video displays usable with a computing device of FIG. 2. Training device 300 is generally configured to be worn on the face of a therapist for use with a patient, and therefore generally comprises features to enable the intended use. In some embodiments, training device 300 is a pair of eyeglasses comprising a frame 310 similar in appearance to the typical frame employed in ordinary eyeglasses. Unlike typical eyeglasses, frame 310 generally includes first and second apertures 312 and 314 for mounting first and second video displays 330 and 340. In some embodiments, frame 310 further includes an undulating portion 316 as found in ordinary frames so as to fit onto the bridge of a nose. Hingedly mounted to the frame 310 are first and second earpieces 318 and 320 that are intended to fit over the ears of the therapist to hold the training device 300 onto the therapist's face. In some embodiments, earpieces 318 and 320 are elongated and are connected to frame 310 by hinges 322.

In general, frame 310 and earpieces 318, 320 of training device 300 are configured to position first and second video displays 330 and 340 over the eyes of the therapist when worn. Accordingly, frame 310 may comprise any design, shape and/or components compatible with this intended use. For example, in some embodiments a frame may be provided which includes a single aperture for receiving a single video display, wherein the single video display covers at least one eye of the therapist when worn (not shown). In some embodiments, earpieces 318 and 320 may be rigidly coupled to frame 310, and/or may comprise an adjustable strap, or a band, such as an elastic band.

In some embodiments, device 300 further includes an integrated "on-device" video display controller 350 that is operably connected to video displays 330 and 340 and which is configured to display and change various images and videos. In some embodiments, display controller 350 is separate from device 300, wherein device 300 is configured to link to display controller 350 by a wired or wireless connection. Display controller 350 may obtain the images from various sources including mobile devices, directly from the internet or other computer network, or from local or remote storage. Display controller 350 may further include other circuit elements for controlling video displays 330 and 340, such as controller circuits, memory, I/O interfaces, and a power source. Frame 310 further comprises various circuitry (not shown) by which video displays 330 and 340 are operable connected to display controller 350 and other electronic components of device 300.

Displays 330 and 340 each generally comprise a transparent video display having a front, forward-facing, or patient side comprising a display surface that is viewable by a patient while a therapist is wearing the training device. Displays 330 and 340 each further comprise a back, rear-facing, or therapist side that is located opposite the patient side of the display and positioned in close proximity to the therapist's face when worn.

Displays 330 and 340 may comprise any display technology compatible with the teachings of the present invention, including but not limited to LED, LCD, OLED, ELD, E ink, HPA, TFT, OTFT, DLP, SED, FED, Laser TV, carbon nanotubes, IMOD, DMS, AMOLED, PDP, quantum dot displays, and the like. In one embodiment, at least one of displays 330 and 340 comprise a high-transparency LED display based on the technology disclosed in United States Patent Application Publication No. 2012/0168789, which incorporated herein by reference, in its entirety. In one embodiment, at least one of displays 330 and 340 comprise a transparent display based on the technology disclosed in at least one of U.S. Pat. Nos. 7,884,784 and 9,865,224, and United States Patent Application Publication Nos. 2018/0367756, 2018/0096642, 2018/0020210, 2018/0004059, 2014/0166991, and 2013/0010208, each of which is incorporated herein in its entirety. Those skilled in the art will appreciate that present or future display technology may be employed without departing from the spirit of the present disclosures. In some embodiments, a video display of the present application further comprises one or more anti-reflective coating and/or layer.

In some embodiments, displays 330 and 340 are capable of displaying media content at various levels of opacity, as defined herein, wherein each level of opacity directly affects or determines a level of transparency for each display. For example, if the opacity level or percentage of media content reproduced on a video display of the present invention is set to approximately 30% opacity, then the transparency level or percentage of the video display will be approximately 70%. Thus, there exists an inverse relationship between an opacity level of media content being reproduced on a video display and a transparency level of the video display. It should be noted that transparency levels or percentages are based on a maximum attainable transparency for the video display when the opacity level or percentage is 0%. Thus, a transparency percentage of 100% does not represent conditions of 0% light scattering, rather is represents whatever amount of light scattering is present when the opacity level of media content is 0% (i.e., no media content is being reproduced on the video display).

In some embodiments, displays 330 and 340 further comprise one or more windows through which the therapist may view the patient while wearing training device 300. For example, in one embodiment at least one of displays 330 and 340 include a window comprising one or more physical holes or openings passing through a thickness of the display. In another embodiment, at least one of displays 330 and 340 include a window comprising one or more areas that are devoid of any pixels or other components, such that the window consists essentially of a transparent material, such as a glass or polymer material. For some embodiments, a transparency of the one or more windows is constant. In some embodiments, a transparency of the one or more windows is variable and/or adjustable.

In some embodiments, training device 300 further comprises eye tracking capabilities, wherein device 300 includes software and electronics for tracking and collecting eye data from a patient during use of device 300. In some embodiments, device 300 comprises one or more video cameras 370 embedded within or otherwise coupled to device 300 in a position that allows device 300 to track the position and movement of the patient's eyes during use of device 300. In some embodiments, device 300 comprises eye tracking software configured to collect and analyze eye data. In some embodiments, device 300 further comprising software for automatically adjusting a transparency of video displays 330 and 340 and/or automatically adjusting an opacity of media content reproduced thereon in response to eye data collected by device 300. In some embodiments, an eye tracking software of device 300 is further capable of adjusting one or more parameter or setting of video displays 330 and 340. In some embodiments, device 300 comprises eye tracking capabilities based on technology disclosed in U.S. Pat. No. 9,958,941, which is incorporated herein by reference, in its entirety.

In some embodiments, the eye tracking capabilities of device 300 produces eye data which is used by device 300 to adjust one or more parameters or settings of displays 330 and 340. For example, eye data may be used by device 300 to adjust an opacity of media content being reproduced on one or more displays of device 300. Eye data may further be stored in on-board memory of device 300, or transmitted to a remote server or memory module for subsequent analysis. In some embodiments, eye data is transmitted to and stored in a cloud server. In some embodiments, the eye data is transferred wirelessly.

Therapeutic training device 300 may further comprise various electronic and non-electronic features and elements which are desirable to provide one or more features of the present invention. For example, in some embodiments device 300 further comprises on on-board power supply, an on-board video processor, on-board memory, on-board wireless transmitter, and various ergonomic features to improve comfort while wearing the device. One having skill in the art will appreciate that the size and shape of frame 310 and displays 330, 340 may be selected based upon a desired use of device 300. For example, in some embodiments displays 330 and 340 are increased and the thickness of frame 310 is decreased to prevent an obstruction of view for either the therapist or the patient. In some embodiments, frame 310 is incorporated into displays 330, 340 such that a "rimless" appearance is achieved for device 300.

Figure 4A:
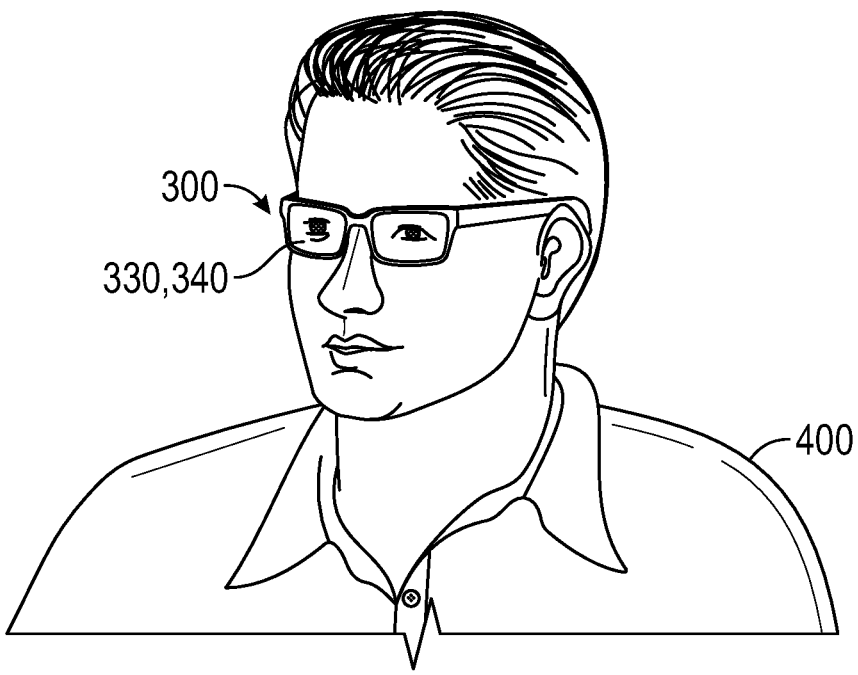
FIG. 4A illustrates a perspective view of a therapeutic training device of the present invention as worn by a therapist, wherein the video displays of the device are substantially transparent in accordance with a representative embodiment of the present invention.
Figure 4B:
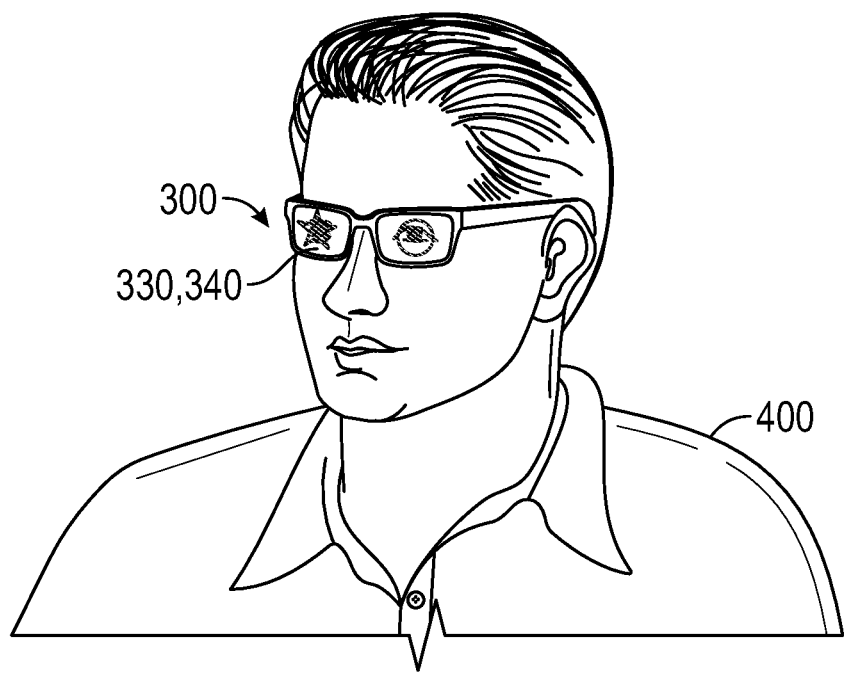
FIG. 4B illustrates a perspective view of a therapeutic training device of the present invention as worn by a therapist, wherein the video displays of the device are partially transparent and media content on the video displays of the device are partially opaque in accordance with a representative embodiment of the present invention.
Figure 4C:
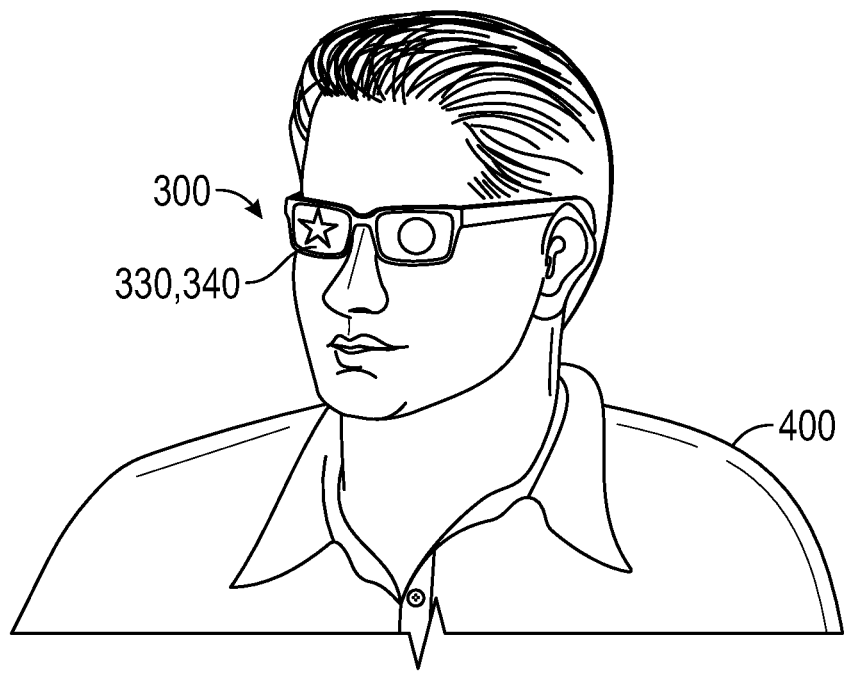
FIG. 4C illustrates a perspective view of a therapeutic training device of the present invention as worn by a therapist, wherein the media content on the video displays is substantially opaque in accordance with a representative embodiment of the present invention.

Referring now to FIGS. 4A-4C, a demonstration of the adjustable properties or settings of displays 330 and 340 is shown. With reference to FIG. 4A, a therapist 400 is shown wearing therapeutic training device 300 wherein the opacity level or percentage of media content on the displays is approximately 0%, whereby the transparency level of the displays is approximately 100%. In this configuration, the eyes of the therapist 400 may be easily viewed through displays 330 and 340. In some embodiments, the configuration of displays 330 and 340 represented in FIG. 4A would appear optically clear, such that there would be nothing obstructing the patient's view of the therapist's eyes.

With reference to FIG. 4B, a therapist 400 is shown wearing device 300 wherein the opacity level or percentage of media content (i.e., a round shape and a star shape) on the displays is approximately 50%, whereby the transparency level of the displays is approximately 50%. In this configuration, the eyes of the therapist 400 are partially occluded or obscured by the media content reproduced on the displays. Conversely, in this configuration the media content reproduced on the displays is partially obscured by the amount of the therapist's eyes that is viewable through the partially-opaque media content. In some embodiments, the media content being reproduced on the displays 330 and 340 represented in FIG. 4B would appear somewhat faded and the therapist's eyes would be detectable through the media content.

With reference to FIG. 4C, a therapist 400 is shown wearing device 300 wherein the opacity level or percentage of media content on the displays is approximately 100%, whereby the transparency level of the displays is approximately 0%. In this configuration, the eyes of the therapist 400 are completely occluded or masked by the media content reproduced on the displays. In some embodiments, the media content being reproduced on the displays 330 and 340 represented in FIG. 4C would appear fully clear and the therapist's eyes would not be visible to the patient.

Figure 5:
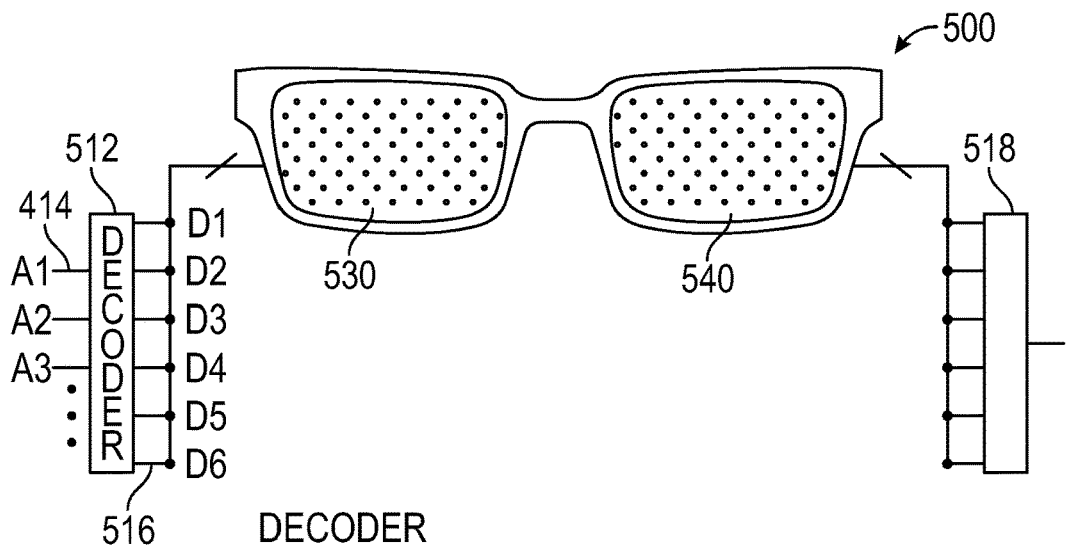
FIG. 5 illustrates a front plan view of a therapeutic training device with configurable video displays in accordance with a representative embodiment of the present invention.

Referring now to FIG. 5, a non-limiting example of logical pixel mapping of displays 530 and 540 of therapeutic training device 500 is shown. In various embodiments, video displays 530 and 540 include many display elements or pixels (shown as dots) that are individually addressable. Coupled with the displays are pixel addressing circuits 512 for video display 530, having input address lines 514 (e.g., A1-A3) and decoded output address lines 516 (e.g., D1-D6). In some embodiments, video display 540 is also operable coupled to addressing circuit 512. In other embodiments, video display 540 is operably coupled to a separate addressing circuit 518.

In various embodiments, video displays 530 and 540 are physically separate displays. In other embodiments, displays 530 and 540 are physically a single piece or connected while being electrically separate and controlled independently of each other. In some embodiments, displays 530 and 540 are physically two separate pieces that are electrically connected and controlled as a single display, thus a singular media content is reproduced across both displays as though they were a single display.

Pixel addressing may be accomplished using decoders that take a number of input address lines and decode the input combination into one of many output signals. Decoders are well-known in the art. Any other techniques known in the art for memory addressing may also be utilized. In some embodiments, the pixels are arranged in a logical grid, not necessarily a physical square or rectangular grid, in which each pixel is at the intersection of a row and a column signal. When the corresponding row and column signals are activated, the pixel at the intersection also becomes active or turned ON, thus displaying one pixel in a larger image.

In some embodiments, the pixel addressing apparatus may include a number of other components in addition or in place of decoders, such as buffers, shift registers, other memory, display processor, and the like. This apparatus may include a combination of hardware and software or firmware. In some embodiments, each display is supplied with image data from a corresponding memory segment. When a memory segment is loaded with image data, the image data may be transferred to the display via pixel address and data lines for display. Address lines, control lines, and data lines are generally known in the art as buses that connect different components in a computing system, as described with respect to FIG. 2. In some embodiments, the display segments may be dynamically configured to be mapped to different address lines and corresponding display memories to show different images accordingly. For example, if the image of a red flower and a blue flower were being displayed on the left and right video displays, respectively, re-configuring the display segments may cause the red flower to be displayed on the right side and the blue flower on the left side by reprogramming the pixel address lines and swapping the corresponding display memories.

In various embodiments, the video displays 530 and 540 may have irregular shapes to fit within the apertures of frame 510, or comprise a plurality of smaller video displays where are electrically coupled to provide a display having a desired shape.

Figure 6:
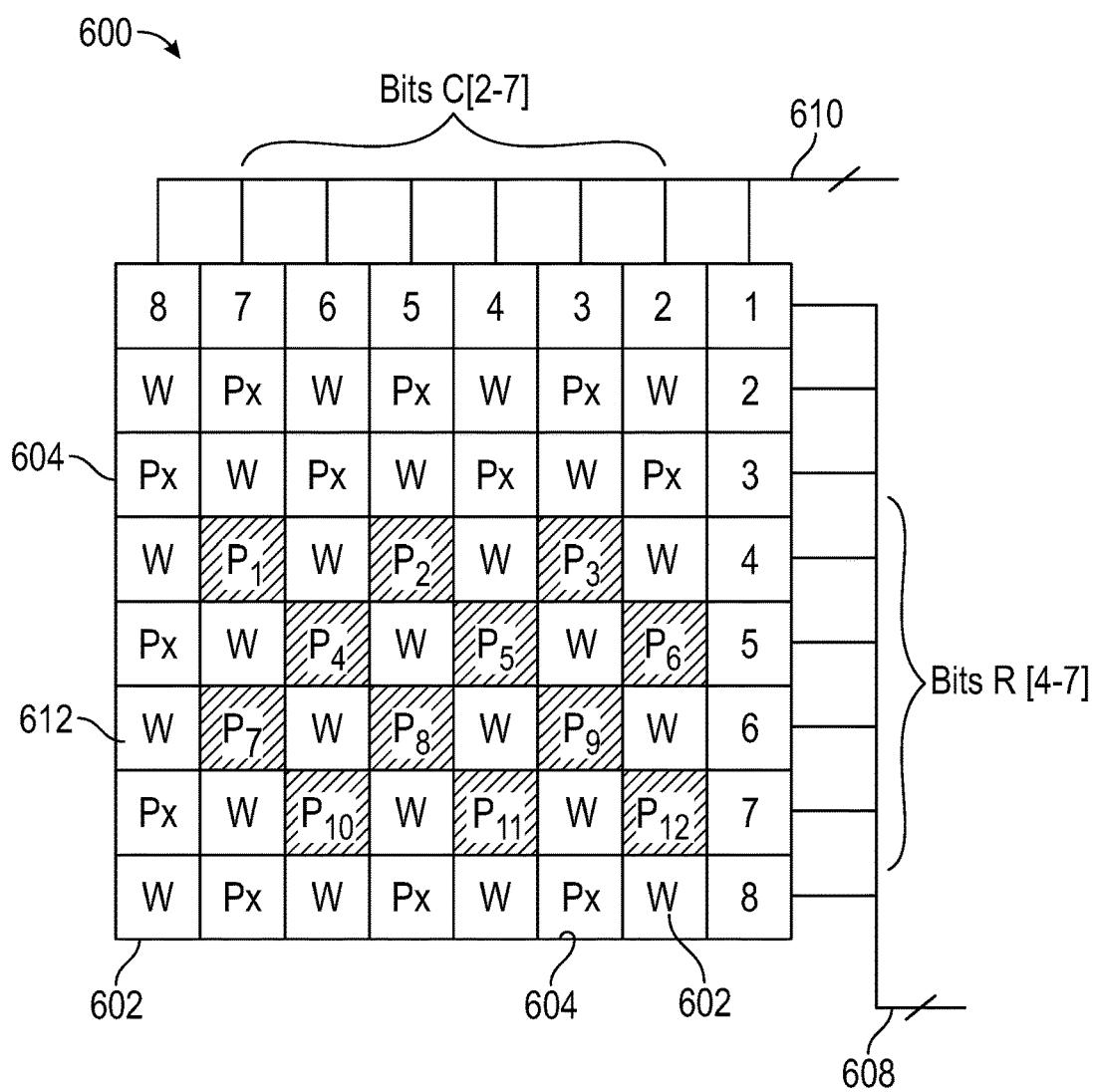
FIG. 6 illustrates a diagram showing an example of pixel mapping for a video display in accordance with a representative embodiment of the present invention.

With reference to FIG. 6, an example pixel grid with address lines for individual pixel addressing is shown. In various embodiments, video display 600 includes a grid 602 having various pixels 604, various windows 612 row buses 608 and column buses 610, each bus including address, control, and data lines. In some embodiments, pixels 604 and windows 612 are evenly interspaced, as shown. In some embodiments, pixels 604 and windows 612 are unevenly distributed. For example, in some embodiments windows 612 are grouped together near a center of display 600 such that windows 612 approximately correspond to a position of the therapist's pupil when the therapeutic training device comprising display 600 is worn by the therapist. A non-limiting example of a pixel grid is shown having a subset of activated pixels 606 corresponding to pixels $P_1$ to $P_{12}$ in row bits 2-7 and column bits 4-6, wherein the activated pixels are at locations (i.e., (column,row)) (7,4), (7,6), (6,5), (6,7), (5,4), (5,6), (4,5), (4,7), (3,4), (3,6), (2,5) and (2,7), wherein inactivated pixels ($P_x$) are at locations (8,3), (8,5), (8,7), (7,2), (7,8), (5,2), (5,8), (3,2), 3,8), and (2,3), and wherein windows (W) are at locations (8,2), (8,4), (8,6), (8,8), (7,3), (7,5), (7,7), (6,2), (6,4), (6,6), (6,8), (5,3), (5,5), (5,7), (4,2), (4,4), (4,6), (4,8), (3,3), (3,5), (3,7), (2,2), (2,4), (2,6), and (2,8).

In various embodiments, to display an image, data from display memory is transferred to pixels selected by row and column bits, such as pixels in area 606. Those skilled in the art appreciate that the various bits in address, control, and data buses (collectively called signals, lines, or bits) are enabled under program or circuit control to cause orderly transfer of data from memory to display. The logical and physical arrangement of pixels P1-P12 shown in area 606 may be reconfigured as desired to accomplish one or more objectives of the current invention.

Referring now to FIGS. 7A-7D, in some embodiments, a therapeutic training device 700 is shown with configurable video displays usable with a computing device of FIG. 2. Training device 700 is generally configured to be worn on the face of a therapist for use with a patient, and therefore generally comprises features to enable the intended use. Similar to therapeutic training device 300 described above, in some embodiments, training device 700 is a pair of eyeglasses comprising a frame 710. Frame 710 generally includes at least one screen, typically a first and second screen 712 and 714 and at least one video display but generally two video displays 730 and 740. In some embodiments, frame 710 further includes a nose support 716 as found in ordinary frames so as to fit onto the bridge of a nose and a first and second earpieces 718 and 720 that are intended to fit over the ears of the therapist to hold the training device 700 onto the therapist's face. In some embodiments, earpieces 718 and 720 are adjustable so as to fit to the comfort of the therapist and the earpieces 718 and 720 may be extended, shortened, or adjusted laterally by any suitable means.

In general, frame 710 and earpieces 718, 720 of training device 700 are configured to position first and second screens 712 and 714 directly over the eyes of the therapist when worn. Accordingly, frame 710 may comprise any design, shape and/or components compatible with this intended use. In some embodiments, the first and second video displays 730 and 740 may be mounted to the frame 710 in an orientation such that a display of media content is emitted from the video displays in a plane perpendicular to the line of sight of the therapist and/or a viewable pathway through the screen. As an example, when the eyeglasses are worn by the therapist, the video display may face down. In some embodiments the video display may face up. In some embodiments, a video display of the present invention is mounted to a hood 722 portion of the frame 710, wherein a mounting surface of the hood is parallel to the line of sight of the therapist, and perpendicular to a plane in which a display of media content is emitted from the video display. In some embodiments, the line of sight of the therapist and/or viewable pathway through the screen is in a first horizontal plane, a mounting surface of the video display is in a second horizontal plane that is generally parallel to the first horizontal plane, and a display of media content is emitted from the video display in a vertical plane that is generally perpendicular to the first and second horizontal planes.

The video displays 730,740 may display and change various images and videos as controlled by a display controller 750 that may be integrated into the frame 710 or may be separate from device 700 wherein device 700 is configured to link to display controller 750 by a wired or wireless connection.

As described above with device 300, display controller 750 may obtain the images from various sources including mobile devices, directly from the internet or other computer network, or from local or remote storage. Display controller 750 may further include other circuit elements for controlling video displays 730 and 740, such as controller circuits, memory, I/O interfaces, and/or a power source. Frame 710 further comprises various circuitry (not shown) by which video displays 730 and 740 are operable connected to display controller 750 and other electronic components of device 700.

Screens 712 and 714 may be configured to receive and reflect media content emitted or otherwise projected from video displays 730 and 740 such that the display of media content is viewable by a patient when the training device 700 worn on the face of a therapist. In some embodiments, screens 712 and 714 comprise a one-way mirror having a reflective coating that faces video displays 730, 740 at approximately 45°, and a see-through side that faces the eyes of the therapist at approximately 45° when worn. The reflective coating is configured to reflect outwardly to the patient any media content displayed on video display 730, 740. When the therapist's face is lighted, the reflective coating becomes transparent such that the patient may view the therapist's face through screens 712, 714, as discussed below.

Screens 712 and 714 may comprise any material or combination of materials compatible with the present invention. In some embodiments, screens 712 and 714 comprise a beamsplitter mirror. In some embodiments, the beamsplitter mirror may be a dielectric mirror. In some instances, a beamsplitter mirror is a polarizing beam splitting mirror. In some instances, a beamsplitter mirror is a non-polarizing beam splitting mirror. Generally, one side of a beamsplitter mirror is coated with an anti-reflective (AR) coating, and the opposite side is coated with a mirror coating. In some instances, at least one of the AR and mirror coatings is dielectric. In some instances, the AR and mirror coatings are both dielectric. AR and mirror coatings compatible for use in the present invention may include single or multiple layers. The mirror coating is configured to provide high reflectance without degrading the picture quality of video displays 730 and 740. Each of the screens 712 and 714 may include a beamsplitter mirror.

Video displays 730 and 740 in combination with screens 712, 714 function as a video display 725, and is herein understood to describe the reflected image of the media content viewable to, or perceivable by a patient. Generally, with video displays 730,740 facing down, screens 712,714 may be at a 45° angle with respect to video displays 730,740 and also with respect to the eye line of the therapist. The angle of screens 712,714 may be adjustable such that the screen is reflected and is viewable by a patient while a therapist is wearing the training device 700. Thus the angle may be greater than or less than 45° as required to align the reflection to be viewable by the patient. Even though the screens 712 and 714 are configured to be at an angle to the eye line of the therapist, screens 712, 714 provide a viewable pathway through the screens and through the reflected video display. In some embodiments, a transparency of the one or more screens 712, 714 is variable and/or adjustable, as discussed in connection with various embodiments of the present invention.

Similar to device 300 described above, video displays 730 and 740 may comprise any display technology compatible with the teachings of the present invention, including but not limited to LED, LCD, OLED, ELD, E ink, HPA, TFT, OTFT, DLP, SED, FED, Laser TV, carbon nanotubes, IMOD, DMS, AMOLED, PDP, quantum dot displays, and the like. In some embodiments, video displays 730 and 740 comprise a video projector, such as a pico projector, a DLP projector, an LED projector, an LCD projector, an LCoS projector, and the like. Those skilled in the art will appreciate that present or future display technology may be employed without departing from the spirit of the present disclosures.

In some embodiments, video displays 730 and 740 are capable of emitting, projecting, or otherwise displaying media content at various levels of brightness and/or opacity, as defined herein, wherein each level of brightness and/or opacity directly affects or determines a level of transparency of the media content displayed on screens 712 and 714. For example, if the opacity level, brightness or percentage of media content reproduced on a screen of the present invention is set to approximately 30% of total brightness and/or opacity, then the level of transparency, brightness or percentage of the video display 725 will be approximately 70%. Thus, there exists an inverse relationship between the brightness, opacity or percentage levels of media content being reproduced on video displays 730, 740 and a transparency level of the media content on screens 712, 714, as perceived by a patient.

Figure 7A:
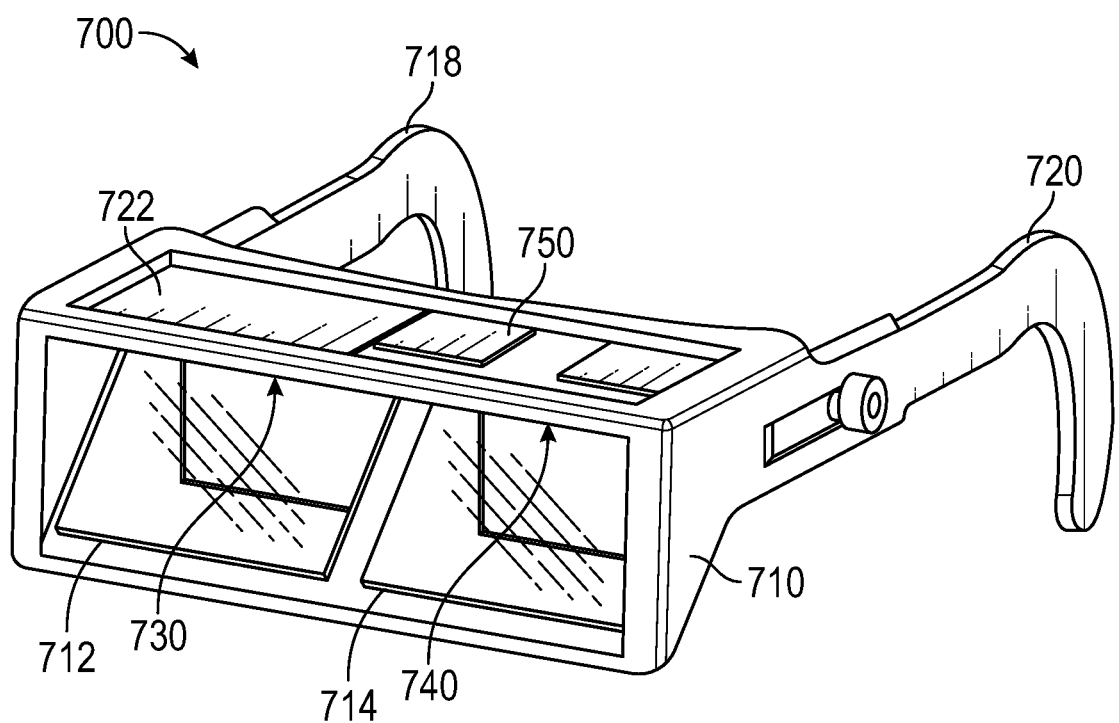
FIG. 7A illustrates a perspective view of a therapeutic training device in accordance with a representative embodiment of the present invention.
Figure 7B:
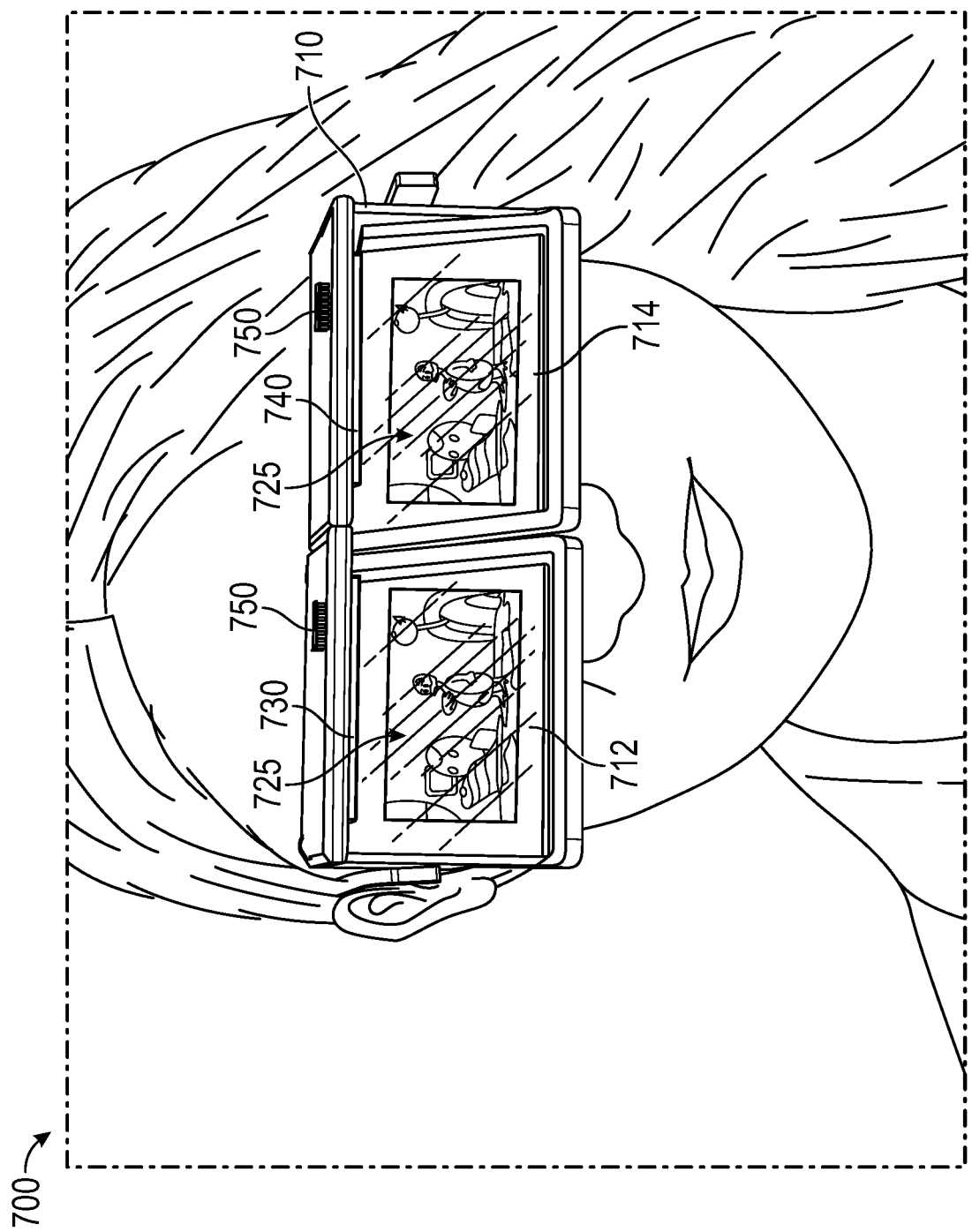
FIG. 7B illustrates a perspective view of a therapeutic training device of the present invention as worn by a therapist, wherein the screens of the device are substantially transparent in accordance with a representative embodiment of the present invention.
Figure 7C:
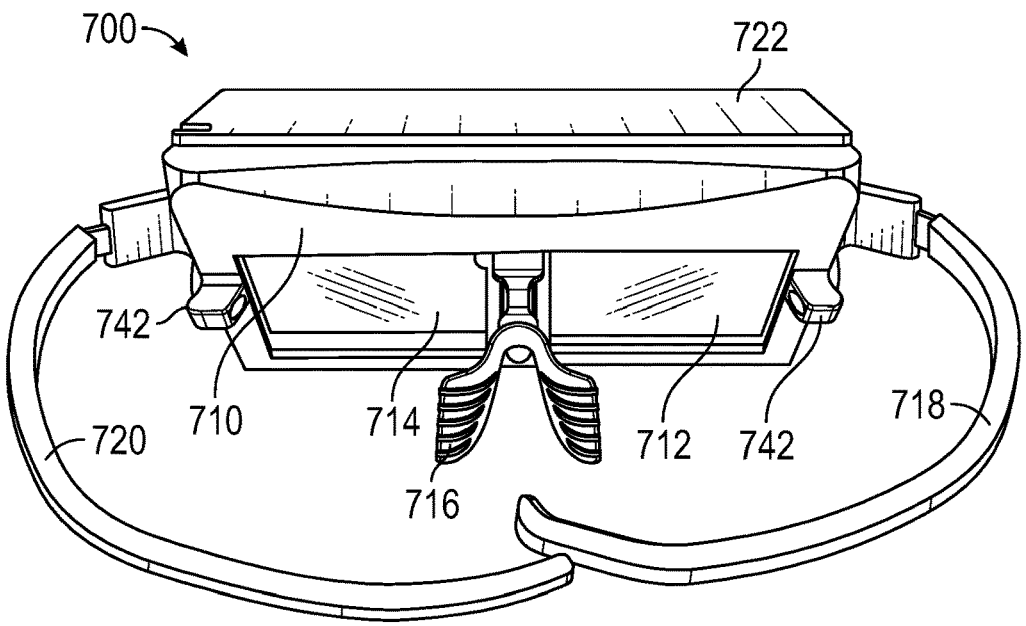
FIG. 7C illustrates a perspective view of a therapeutic training device in accordance with a representative embodiment of the present invention.
Figure 7D:
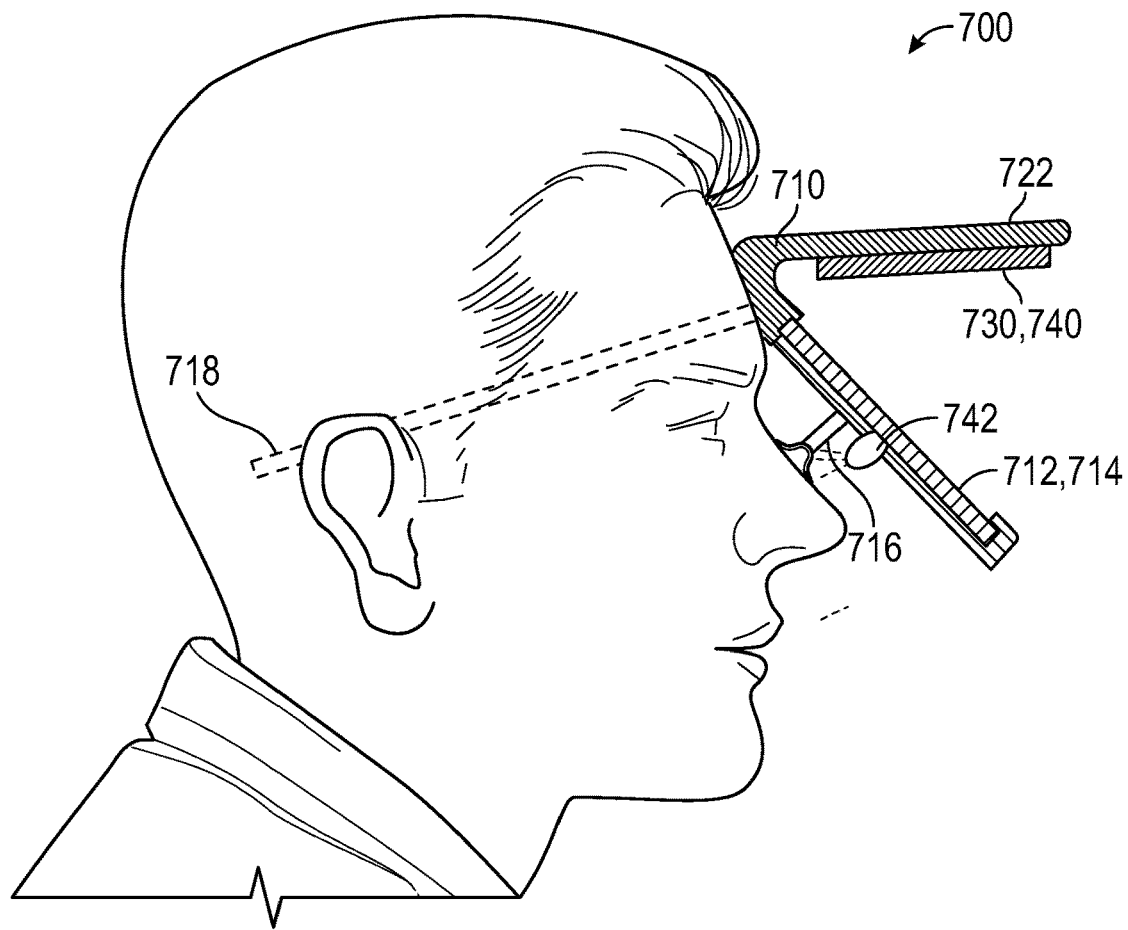
FIG. 7D illustrates a side view of a therapeutic training device of the present invention as worn by a therapist in accordance with a representative embodiment of the present invention.

Referring now to FIGS. 7C-7D, in some embodiments, the frame 710 may be configured to rest directly on the forehead of the user and secured by earpieces 718 and 720 and further balanced with nose support 716. Various embodiments may include at least one light 742. In some embodiments, the light may be coupled to the frame 710 and directs light to the face of the therapist or wearer of the therapeutic training device 700. The light may include several lights located on the bottom or surrounding the frames in locations best suited to illuminate the face, and in particular the eyes of the therapist. For example, the lights may be several LCDs located along the bottom of the frame 710. In some embodiments, the brightness of the light 742 may be adjustable. In various embodiments, when a brightness or opacity of media content on video displays 730 and 740 is varied, so is a brightness of light 742. In some instances, the brightness level of video displays 730 and 740 is inverse to a brightness level of light 742.

In some embodiments, when the level of brightness of media content on video displays 730, 740 and or screens 712, 714 is adjusted, the luminosity or brightness of the light 742 is adjusted accordingly. A therapist may be wearing therapeutic training device 700 wherein the brightness level or percentage of media content on the displays is approximately 0%, whereby the transparency level of the screens is approximately 100% and the brightness of the light 742 is also approximately 100%. In this configuration, the eyes of the therapist may be easily viewed through screens 712 and 714. In some embodiments, the configuration of the screens 712 and 714 would appear optically clear with sufficient illumination, such that there would be nothing obstructing the patient's view of the therapist's eyes through screens 712, 714. As another example, if the brightness level or percentage of media content reproduced on video display 730, 740 (the reflection of which is viewable on screen 712,714) is set to approximately 30% opacity, then the brightness of the light will be approximately 70%. The light 742 may be changed to various levels of brightness as controlled by display controller 750 that may be integrated into the frame 710 or may be separate from device 700, wherein device 700 is configured to link to display controller 750 by a wired or wireless connection.

Referring now to FIG. 7E, an example display controller 750 is shown. In various embodiments, a therapeutic training device of the present invention may include a display controller 750 which may be embedded within a surface of the training device, or which may be separate from the training device and operably connected thereto by various means. In some embodiments, display controller 750 comprises an embedded controller board 752 including a power source 754, an Input/Output (I/O) module 756, a Network Interface Card (NIC) 758, memory 760, and a Central Processing Unit (CPU) 762 all connected via electronic signal busses for data transfer and control.

In various embodiments, controller board 752 is a thin circuit with minimal power requirements to download media content data from an external source via NIC 758, store in memory 760, convert media content data to display format for one or more video displays of the training device, transfer formatted media content data onto one or more video displays of the training device via the I/O module 756 and drive the video display(s) on the training device for actual display.

In various embodiments, the power source may be a small battery, a rechargeable battery or capacitor, or other suitable power source. In some embodiments, the power source is a battery pack that is connected to the training device via power cord. In some embodiments, the training device is powered directly from a wall receptacle using a plug-in transformer.

In various embodiments, the NIC may be in contact with an external source, such as a mobile computing device like a cellphone or tablet, or a larger computer, the internet, and the like, to download media content. In some embodiments, the NIC may be used during an initialization period to preload any images or video to display and then stop data acquisition until a next session as determined and controlled by a user (for example, by pressing a button to activate new data acquisition), or by the training device being turned OFF and ON again. In other embodiments, the NIC may continuously be connected to a data source download new data while the training device is in use, so it can update media content in real time. In some embodiments, the NIC may be part of an IOT (Internet Of Things) system with its own IP address directly connected to the Internet to download images from a predetermined website or multiple websites the addresses (URL) of which may be embedded in the display controller. In some embodiments, the NIC may be connected by wireless, such as WiFi, or wired, such as USB, links to a device, such as a smartphone.

In various embodiments, the controller board 752 may perform all or some of the formatting of the media content to be displayed on the device. It may further include software and/or firmware that performs other signal and image processing, such as filtering, color change, animation (including image fading in and out), scaling and/or truncating media content, stretching, and the like. In some embodiments, the embedded software may adjust the opacity of the media content. In some embodiments, the embedded software may track and record eye data of the patient during use of the device. In some embodiments, the embedded software may adjust the opacity of the media content and/or brightness of lights in response to eye data. In some embodiments, the embedded software may upload eye data to remote server, such as a cloud server.

Referring now to FIG. 8, an example I/O processor 870 is shown in communication with a display controller separate from the training device (not shown). In various embodiments, the therapeutic training device includes a limited control circuit 872 with an I/O module 874 to transfer media content data, and an antenna 876 for receipt and/or transmission of radio waves 878.

In various embodiments, a power source, such as a small battery or a rechargeable battery or capacitor (not shown) or other suitable power source may be used to power the circuit.

In various embodiments, the rest of the circuit needed to control the video displays of the training device may be located off the training device and in another location, such as a belt unit carried by the user. Such belt unit may include a NIC that may be in contact with an external source, such as a mobile computing device like a cellphone or tablet, or a larger computer, the internet, and the like, to download new images. The NIC may also be in contact with the antenna 876 to transmit and/or receive data from to/from the limited control circuit 804 via wireless communications or a hardwired interface, such as a mini USB. In some embodiments, the belt unit includes the components needed to download and format images from external sources, similar to the components shown in FIG. 7. In various embodiments, the NIC may be used during an initialization period to preload any media content to display and then stop data acquisition until a next session as determined and controlled by a user (for example, by pressing a button to activate new data acquisition), or by the training device being turned OFF and ON again. In other embodiments, the NIC may continuously be connected to a data source to download new media content data while the device is in use, so it can update displayed media content in real time. In some embodiments, the NIC may be part of an IOT (Internet Of Things) system with its own IP address directly connected to the Internet to download images from a predetermined website or multiple websites the addresses (URL) of which may be embedded in the display controller. In some embodiments, the NIC may be connected by wireless, such as WiFi, or wired, such as USB, links to a device, such as a smartphone. In various embodiments, the formatting of the media content takes place on the belt.

Referring now to FIG. 9, an example training device 900 is shown in communication with a mobile computing device 916 via a receiver 910. In various embodiments, a training device 900 of the present invention is in contact with a transmitter/receiver 910 via an interface 912 to receive wireless signals 908 from a smartphone 904 running an app (small mobile software application) 906 usable to download media content to the training device.

In various embodiments, the training device 900 may be similar to the training device of FIG. 8, in which a small local circuit is deployed within the training device to receive and display the media content data after formatting (if any). In an illustrative operation, the app 906 running on smartphone 904 may transmit media content data via wireless signals to the receiver 910. The receiver 910 may include other processing components, such as CPU and memory to format the transmitted image for display on at least one video display of the training device via interface 912. Interface 912 may be wired, such as USB or wireless signals such as WiFi, NFC (Near Field Communication), Bluetooth, or other similar wireless protocols. In these embodiments, the receiver/computing unit 910 may receive standard media content from the smartphone and then format it for display on the training device. In other embodiments, the training device may include video displays without any processing components. In such embodiments, the formatted media content is directly displayed via data and control busses contained within the device 910.

In some embodiments, app 906 may download a standard format media content, such as MP4, 3GP, .MOV, .f4, JPEG, bitmap, and the like, from the Internet and then format it for display on the training device before transmitting it to the receiver for display on one or more video displays of the training device. The app may include additional interfaces for defining the configuration of video display for formatting. For example, the app may include settings whereby a user may set or adjust a location on the video display for display of the formatted media content. It may also include options for the user to select various animation modes, playback modes, or other modification to be displayed on the training device. Such selections may be performed during a setup session before activating or using the training device.

Figure 10:
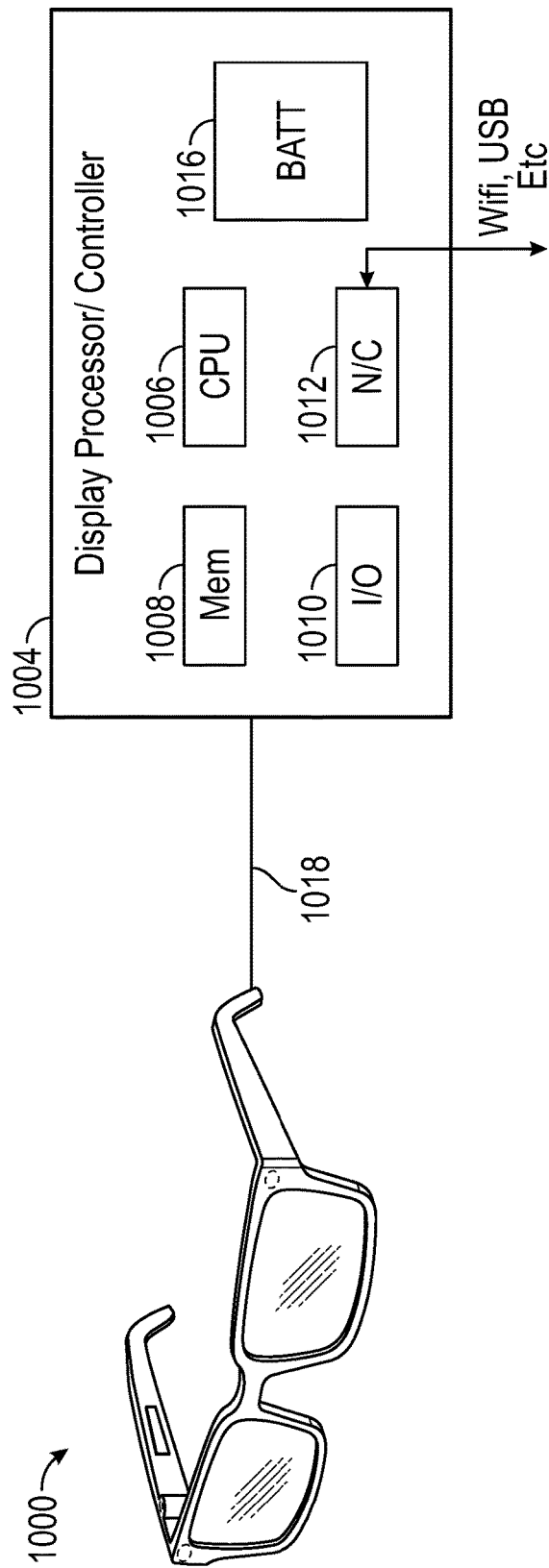
FIG. 10 illustrates a therapeutic training device coupled with a remote display controller in accordance with a representative embodiment of the present invention.

Referring now to FIG. 10, an example therapeutic training device 1000 is shown coupled with a separate display control unit 1004. In various embodiments, a therapeutic training device 1000 of the present invention may be in contact with an external display controller board/unit 1004, via an interface 1018 to receive media content data for display. The controller board 1004 may include various computing components such as a CPU 1006, memory 1008, I/O module 1010, NIC module 1012, and power supply 1016.

In various embodiments, the training device receives media content data via interface 1018 and does not perform any processing locally and does not need a local power supply.

In some embodiments, display processor/controller 1004 may be preprogrammed to format media content for the particular training device it is coupled to. It may include firmware or downloadable programs to perform all the video formatting and/or manipulation necessary to display the final form of the media content and its effects (such as opacity, discussed herein). The controller 1004 may further include a NIC interface 1012 for connecting to data sources such as computers, tablets, smartphones or directly to the internet to download media content data. The NIC module as well as mask interface 1018 may be wired, such as USB, or wireless such as WiFi, NFC (Near Field Communication), Bluetooth, or other similar wireless protocols. In these embodiments, the display controller 1004 may receive standard media content from various sources and then format them (if needed) to generate media content for display on the training device 1000.

Figure 11:
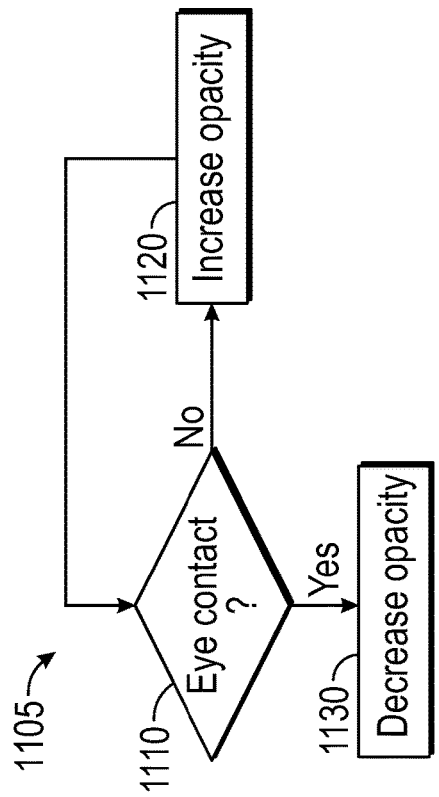
FIG. 11 illustrates a diagram showing a method for using a therapeutic training device in accordance with a representative embodiment of the present invention.

Referring now to FIG. 11, an example of a method 1105 for using the therapeutic training device of the present invention is shown. In general, the training device of the present invention is designed and intended to assist a therapist in developing muscle memory in a patient, and specifically to train a patient to make and maintain eye contact with the therapist. According, a first step 1110 in a method for using the training device is to determine if the patient is making eye contact with the training device, and specifically with one or more video displays of the training device. In some embodiments, step 1110 is performed manually by the therapist. In some embodiments, step 1110 is performed via eye tracking components and software of the training device. If it is determined that the patient is not making eye contact with the training device, an opacity of media content displayed on the training device is increased (step 1120). If it is determined that the patient is making and/or maintaining eye contact with the training device, an opacity of media content displayed on the training device is decreased (step 1130). The steps of this method are repeated throughout a training session with the therapeutic training device of the present invention.

It will be understood that each step of the processes and methods described above, and combinations of steps, may be implemented by computer program instructions. These program instructions may be provided to a processor to produce a machine, such that the instructions, which execute on the processor, enable implementing the actions specified. The computer program instructions may be executed by a processor to cause a series of operational steps to be performed by the processor to produce a computer implemented process such that the instructions, which execute on the processor to provide steps for implementing the actions. The computer program instructions may also cause at least some of the operational steps to be performed in parallel. Moreover, some of the steps may also be performed across more than one processor, such as might arise in a multi-processor computer system. In addition, one or more steps or combinations of steps described may also be performed concurrently with other steps or combinations of steps, or even in a different sequence than described without departing from the scope or spirit of the disclosure.

Accordingly, steps of processes or methods described support combinations of techniques for performing the specified actions, combinations of steps for performing the specified actions and program instruction for performing the specified actions. It will also be understood that each step, and combinations of steps described, can be implemented by special purpose hardware based systems which perform the specified actions or steps, or combinations of special purpose hardware and computer instructions.

It will be further understood that unless explicitly stated or specified, the steps described in a process are not ordered and may not necessarily be performed or occur in the order described or depicted. For example, a step A in a process described prior to a step B in the same process, may actually be performed after step B. In other words, a collection of steps in a process for achieving an end-result may occur in any order unless otherwise stated.

Changes can be made to the claimed invention in light of the above Detailed Description. While the above description details certain embodiments of the invention and describes the best mode contemplated, no matter how detailed the above appears in text, the claimed invention can be practiced in many ways. Details of the system may vary considerably in its implementation details, while still being encompassed by the claimed invention disclosed herein.

Particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the claimed invention to the specific embodiments disclosed in the specification, unless the above Detailed Description section explicitly defines such terms. Accordingly, the actual scope of the claimed invention encompasses not only the disclosed embodiments, but also all equivalent ways of practicing or implementing the claimed invention.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The above specification, examples, and data provide a complete description of the manufacture and use of the claimed invention. Since many embodiments of the claimed invention can be made without departing from the spirit and scope of the disclosure, the invention resides in the claims hereinafter appended. It is further understood that this disclosure is not limited to the disclosed embodiments, but is intended to cover various arrangements included within the spirit and scope of the broadest interpretation so as to encompass all such modifications and equivalent arrangements.

EXAMPLES

Example 1: Therapeutic Treatment of Patient with ASD

A patient with ASD is positioned face-to-face with a therapist. A therapeutic training device of the present invention is positioned on the therapist's face so that the therapist's eyes are viewable by the patient through the video displays of the training device. The patient's eye contact is analyzed to determine if the patient is making eye contact with the therapist. This analysis may be done manually by the therapist, or may be automated through the use of eye tracking components and software. If eye contact is not being made and maintained with the therapist, media content is displayed on the video displays of the training device at a level of opacity that results in the patient making eye contact with the video displays. The opacity level of the media content may be adjusted manually by the therapist, or may be adjusted automatically by the training device in response to eye data acquired by eye tracking component and software of the device. If eye contact is being made and maintained with the video displays of the training device, the opacity of the media content is decreased such that the therapist's eyes become viewable to the patient through the media content. As the patient continues to maintain eye contact with the video displays, the opacity of the media content is decreased such that the therapist's eyes are increasingly viewable to the patient. As the patient begins to lose or break eye contact with therapist's eyes and/or the video displays, the opacity of the media content is increased to encourage the patient to reestablish eye contact with the video screens of the training device.

Through this repeated therapy method, the patient develops muscle memory for making and maintaining eye contact with the therapist.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A therapeutic training device, comprising
    an eyeglass frame having an aperture:
    a display positioned within the aperture and comprising an outer surface for displaying media content, and an inner surface that is positioned close to the face of a therapist when worn;
    means for securing the frame and display to a face of a therapist;
    a controller coupled to the display to control the display of media content on the outer surface of the display; and
    eye tracking components and software.

2. The device of claim 1, wherein the display further comprises a window.

3. The device of claim 2, wherein the window is a physical opening.

4. The device of claim 2, wherein the window is a portion of the display that is without a pixel.

5. The device of claim 1, wherein an opacity of the media content displayed on the outer surface of the display is adjustable.

6. A therapeutic training device, comprising:
    eyeglass frames;
    a video display positioned within the eyeglass frames;
    a controller coupled to the video display to control a display of media content on the video display;
    a screen configured to reflect the display of media content outwardly such that the display of media content is viewable by a patient when the therapeutic training device is worn by a wearer, wherein a brightness of the video display is adjustable such that a transparency of the screen is variable, and wherein the device further comprises a light having an adjustable brightness to illuminate the eyes of the wearer.

7. The device of claim 6, wherein the video display is mounted in the eyeglass frames in an orientation such that the display of media content is emitted from the video display in a plane that is generally perpendicular to a line of sight through the screen.

8. The device of claim 7, wherein the screen is mounted in the eyeglass frames in a plane approximately 45° to the orientation of the video display.

9. The device of claim 6, wherein the video display is a video projector, a LCD display, a LED display, or a quantum dot display.

10. The device of claim 6, wherein the screen comprises a one-way mirror.

11. The device of claim 6, wherein the screen comprises a dielectric mirror.

12. The device of claim 6, wherein the screen comprises a plurality of screens.

13. The device of claim 6, further comprising a controller configured to inversely adjust brightness levels of the video display and the light.

14. A method for treating a patient with autism spectrum disorder using the therapeutic training device of claim 6, said method comprising steps of:
    positioning the patient face-to-face with a therapist;
    placing the therapeutic training device on the therapist's face;
    displaying to the patient media content on the therapeutic training device;
    observing the patient's eye contact;
    assessing a direction of the patient's eye contact; and
    adjusting a level of the media content.

15. The method of claim 14, wherein the therapeutic training device further comprises eye tracking components and software, and the steps of observing the patient's eye contact and assessing the direction of the patient's eye contact is accomplished by the eye tracking components and software of the therapeutic training device.

16. The method of claim 14, wherein the steps of observing the patient's eye contact and assessing the direction of the patient's eye contact are accomplished manually by the therapist.

17. The method of claim 14, wherein the therapeutic training device further comprises software to adjust the level of the media content, and the step of adjusting the level of the media content is accomplished by the software of the therapeutic training device.

18. The method of claim 14, wherein the step of adjusting the level of the media content is accomplished manually by the therapist.

* * * * *